US011679252B2

(12) United States Patent
Harris et al.

(10) Patent No.: US 11,679,252 B2
(45) Date of Patent: *Jun. 20, 2023

(54) METHODS AND DEVICES FOR ACTIVATING BROWN ADIPOSE TISSUE USING ELECTRICAL ENERGY

(71) Applicant: Cilag GmbH International, Zug (CH)

(72) Inventors: Jason L. Harris, Lebanon, OH (US); Tamara C. Baynham, Bowie, MD (US)

(73) Assignee: Cilag GmbH International, Zug (CH)

( * ) Notice: Subject to any disclaimer, the term of this patent is extended or adjusted under 35 U.S.C. 154(b) by 106 days.

This patent is subject to a terminal disclaimer.

(21) Appl. No.: 17/208,125

(22) Filed: Mar. 22, 2021

(65) Prior Publication Data

US 2021/0205610 A1    Jul. 8, 2021

Related U.S. Application Data

(60) Continuation of application No. 16/445,725, filed on Jun. 19, 2019, now Pat. No. 10,994,123, which is a
(Continued)

(51) Int. Cl.
*A61N 1/04* (2006.01)
*A61N 1/05* (2006.01)
*A61N 1/36* (2006.01)

(52) U.S. Cl.
CPC ......... *A61N 1/0456* (2013.01); *A61N 1/0492* (2013.01); *A61N 1/0502* (2013.01);
(Continued)

(58) Field of Classification Search
CPC .................... A61N 1/0492; A61N 1/0456
(Continued)

(56) References Cited

U.S. PATENT DOCUMENTS 4,498,843 A    2/1985 Schneider et al.
4,578,770 A    3/1986 Mitani
(Continued)

FOREIGN PATENT DOCUMENTS

CN    2045308 U    10/1989
CN    2520883 Y    11/2002
(Continued)

OTHER PUBLICATIONS

"3M CoTran™ 9702 Membrane" Brochure. (2009).
(Continued)

*Primary Examiner* — Catherine M Voorhees
*Assistant Examiner* — Roland Dinga
(74) *Attorney, Agent, or Firm* — Mintz Levin Cohn Ferris Glovsky and Popeo, P.C.

(57) ABSTRACT

Methods and devices are provided for activating brown adipose tissue (BAT) using electrical energy. In general, the methods and devices can facilitate activation of BAT to increase thermogenesis. The BAT can be activated by applying an electrical signal thereto that can be configured to target sympathetic nerves that can directly innervate the BAT. The electrical signal can be configured to target the sympathetic nerves using fiber diameter selectivity. In other words, the electrical signal can be configured to activate nerve fibers having a first diameter without activating nerve fibers having diameters different than the first diameter. Sympathetic nerves include postganglionic unmyelinated, small diameter fibers, while parasympathetic nerves that can directly innervate BAT include preganglionic myelinated, larger diameter fibers. The electrical signal can be configured to target and activate the postganglionic unmyelinated, small diameter fibers without activating the preganglionic myelinated, larger diameter fibers.

20 Claims, 11 Drawing Sheets

Related U.S. Application Data continuation of application No. 16/197,786, filed on Nov. 21, 2018, now Pat. No. 10,391,298, which is a continuation of application No. 16/108,730, filed on Aug. 22, 2018, now Pat. No. 10,207,102, which is a division of application No. 14/584,066, filed on Dec. 29, 2014, now Pat. No. 10,080,884.

(52) U.S. Cl.
CPC ......... *A61N 1/0504* (2013.01); *A61N 1/0551* (2013.01); *A61N 1/36034* (2017.08); *A61N 1/36146* (2013.01); *A61N 1/36189* (2013.01)

(58) Field of Classification Search
USPC .................................................. 607/2, 116
See application file for complete search history.

(56) References Cited

U.S. PATENT DOCUMENTS

| | | |
|---|---|---|
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 4,772,631 A | 9/1988 | Holloway et al. |
| 4,927,836 A | 5/1990 | Holloway et al. |
| 4,937,267 A | 6/1990 | Holloway et al. |
| 4,978,338 A | 12/1990 | Melsky et al. |
| 5,434,184 A | 7/1995 | Holloway et al. |
| 5,453,270 A | 9/1995 | Bills |
| 5,486,359 A | 1/1996 | Caplan et al. |
| 5,724,996 A | 3/1998 | Piunti |
| 5,731,408 A | 3/1998 | Hadley et al. |
| 5,736,396 A | 4/1998 | Bruder et al. |
| 5,789,654 A | 8/1998 | Lowell et al. |
| 5,811,094 A | 9/1998 | Caplan et al. |
| 5,827,735 A | 10/1998 | Young et al. |
| 5,827,740 A | 10/1998 | Pittenger |
| 5,837,539 A | 11/1998 | Caplan et al. |
| 5,837,670 A | 11/1998 | Hartshorn |
| 5,843,723 A | 12/1998 | Dubensky, Jr. et al. |
| 5,911,992 A | 6/1999 | Braswell et al. |
| 6,069,147 A | 5/2000 | Williams et al. |
| 6,071,747 A | 6/2000 | Strosberg et al. |
| 6,072,100 A | 6/2000 | Mooney et al. |
| 6,197,580 B1 | 3/2001 | Susulic et al. |
| 6,207,878 B1 | 3/2001 | Campbell et al. |
| 6,224,873 B1 | 5/2001 | Jones |
| 6,246,912 B1 | 6/2001 | Sluijter et al. |
| 6,381,496 B1 | 4/2002 | Meadows et al. |
| 6,445,955 B1 | 9/2002 | Michelson et al. |
| 6,451,336 B2 | 9/2002 | Sugano et al. |
| 6,475,530 B1 | 11/2002 | Kuhrts |
| 6,532,386 B2 | 3/2003 | Sun et al. |
| 6,565,847 B1 | 5/2003 | Gorsek |
| 6,602,694 B1 | 8/2003 | Albrandt et al. |
| 6,605,297 B2 | 8/2003 | Nadachi et al. |
| 6,620,594 B1 | 9/2003 | Giacobino et al. |
| 6,645,229 B2 | 11/2003 | Matsumura et al. |
| 6,694,185 B2 | 2/2004 | Orton |
| 6,908,987 B2 | 6/2005 | Spiegelman et al. |
| 6,922,590 B1 | 7/2005 | Whitehurst |
| 6,927,288 B2 | 8/2005 | Ito |
| 6,983,753 B1 | 1/2006 | Lenhard et al. |
| 7,060,437 B1 | 6/2006 | Kopchick |
| 7,091,006 B2 | 8/2006 | Spiegelman et al. |
| 7,135,611 B2 | 11/2006 | MacDougald et al. |
| 7,191,007 B2 | 3/2007 | Desai et al. |
| 7,236,830 B2 | 6/2007 | Gliner |
| 7,250,283 B2 | 7/2007 | Spiegelman et al. |
| 7,264,602 B1 | 9/2007 | Longsworth |
| 7,300,409 B2 | 11/2007 | Kopanic, Jr. et al. |
| 7,367,341 B2 | 5/2008 | Anderson et al. |
| 7,396,642 B2 | 7/2008 | Yamaoka et al. |
| 7,440,806 B1 | 10/2008 | Whitehurst et al. |
| 7,476,406 B1 | 1/2009 | Smidt |
| 7,526,061 B2 | 4/2009 | Kobayashi |
| 7,576,052 B2 | 8/2009 | Kahn et al. |
| 7,599,736 B2 | 10/2009 | DiLorenzo |
| 7,599,743 B2 | 10/2009 | Hassler, Jr. et al. |
| 7,599,744 B2 | 10/2009 | Giordano et al. |
| 7,647,112 B2 | 1/2010 | Tracey et al. |
| 7,818,060 B2 | 10/2010 | Torgerson |
| 7,935,073 B2 | 5/2011 | Levine et al. |
| 7,979,137 B2 | 7/2011 | Tracey et al. |
| 8,126,530 B2 | 2/2012 | Bare et al. |
| 8,162,530 B2 | 4/2012 | Lee |
| 8,476,227 B2 | 7/2013 | Kaplan et al. |
| 8,690,934 B2 | 4/2014 | Boyden et al. |
| 8,696,616 B2 | 4/2014 | Baynham et al. |
| 8,812,100 B2 | 8/2014 | Voegele et al. |
| 8,911,701 B2 | 12/2014 | Gaillard et al. |
| 9,044,606 B2 | 6/2015 | Harris et al. |
| 9,662,486 B2 | 5/2017 | Harris et al. |
| 10,080,884 B2 | 9/2018 | Harris et al. |
| 10,207,102 B2 | 2/2019 | Harris et al. |
| 10,391,298 B2 | 8/2019 | Harris et al. |
| 2001/0014815 A1 | 8/2001 | Matsumura et al. |
| 2001/0032337 A1 | 10/2001 | Forman |
| 2002/0016618 A1 | 2/2002 | Da Silva et al. |
| 2002/0123774 A1 | 9/2002 | Loeb et al. |
| 2002/0165586 A1 | 11/2002 | Hill et al. |
| 2003/0082168 A1 | 5/2003 | Yegorova |
| 2003/0104081 A1 | 6/2003 | Rombi |
| 2003/0119775 A1 | 6/2003 | Surwit et al. |
| 2003/0181958 A1 | 9/2003 | Dobak |
| 2003/0212016 A1 | 11/2003 | Gimeno et al. |
| 2003/0220238 A1 | 11/2003 | Adams et al. |
| 2004/0039312 A1 | 2/2004 | Hillstead et al. |
| 2004/0077556 A1 | 4/2004 | Chinery |
| 2005/0043524 A1 | 2/2005 | Bhanot et al. |
| 2005/0045498 A1 | 3/2005 | Purcell et al. |
| 2005/0080026 A1 | 4/2005 | Steuernagel et al. |
| 2005/0136429 A1 | 6/2005 | Guarente et al. |
| 2005/0177067 A1 | 8/2005 | Tracey et al. |
| 2005/0261223 A1 | 11/2005 | Czech et al. |
| 2005/0277998 A1 | 12/2005 | Tracey et al. |
| 2005/0288740 A1 | 12/2005 | Hassler et al. |
| 2006/0004421 A1 | 1/2006 | Bennett et al. |
| 2006/0008540 A1 | 1/2006 | Xiu |
| 2006/0014178 A1 | 1/2006 | Whitson et al. |
| 2006/0084637 A1 | 4/2006 | Alemany |
| 2006/0121158 A1 | 6/2006 | Ferruzzi et al. |
| 2006/0190053 A1 | 8/2006 | Dobak |
| 2006/0195145 A1 | 8/2006 | Lee et al. |
| 2006/0195146 A1 | 8/2006 | Tracey et al. |
| 2006/0195153 A1 | 8/2006 | DiUbaldi et al. |
| 2006/0204599 A1 | 9/2006 | Wheat |
| 2006/0223104 A1 | 10/2006 | Kahn et al. |
| 2007/0055154 A1 | 3/2007 | Torbati |
| 2007/0100387 A1 | 5/2007 | Gerber |
| 2007/0162085 A1 | 7/2007 | DiLorenzo |
| 2007/0185541 A1 | 8/2007 | DiUbaldi et al. |
| 2007/0282318 A1 | 12/2007 | Spooner et al. |
| 2008/0046012 A1 | 2/2008 | Covalin et al. |
| 2008/0080026 A1 | 4/2008 | Mestha et al. |
| 2008/0132962 A1 | 6/2008 | DiUbaldi et al. |
| 2008/0138449 A1 | 6/2008 | Heuer et al. |
| 2008/0139875 A1 | 6/2008 | Tracey et al. |
| 2008/0147146 A1 | 6/2008 | Wahlgren et al. |
| 2008/0262411 A1 | 10/2008 | Dobak |
| 2008/0293830 A1 | 11/2008 | Katagiri et al. |
| 2009/0012555 A1 | 1/2009 | Makower et al. |
| 2009/0018594 A1 | 1/2009 | Laufer et al. |
| 2009/0024144 A1 | 1/2009 | Zeiner et al. |
| 2009/0024192 A1 | 1/2009 | Mulholland |
| 2009/0054487 A1 | 2/2009 | Kolonics et al. |
| 2009/0062193 A1 | 3/2009 | Weyer et al. |
| 2009/0081715 A1 | 3/2009 | Burns-Guydish et al. |
| 2009/0082641 A1 | 3/2009 | Giftakis et al. |
| 2009/0093858 A1 | 4/2009 | DiUbaldi |
| 2009/0118780 A1 | 5/2009 | DiLorenzo |
| 2009/0132018 A1 | 5/2009 | DiUbaldi et al. |

(56) References Cited

U.S. PATENT DOCUMENTS

| | | |
|---|---|---|
| 2009/0149918 A1 | 6/2009 | Krulevitch et al. |
| 2009/0157149 A1 | 6/2009 | Wahlgren et al. |
| 2009/0171375 A1 | 7/2009 | Coe et al. |
| 2009/0202387 A1 | 8/2009 | Dlugos, Jr. et al. |
| 2009/0202659 A1 | 8/2009 | Gimble |
| 2009/0204131 A1 | 8/2009 | Ortiz et al. |
| 2009/0228078 A1 | 9/2009 | Zhang et al. |
| 2009/0306739 A1 | 12/2009 | DiLorenzo |
| 2010/0056433 A1 | 3/2010 | Sensfuss |
| 2010/0056948 A1 | 3/2010 | Hornby et al. |
| 2010/0161001 A1 | 6/2010 | DiUbaldi et al. |
| 2010/0161005 A1 | 6/2010 | Wahlgren et al. |
| 2010/0222734 A1 | 9/2010 | Jayes et al. |
| 2010/0239648 A1 | 9/2010 | Smith et al. |
| 2010/0249677 A1 | 9/2010 | DiUbaldi et al. |
| 2010/0312295 A1 | 12/2010 | Vase et al. |
| 2011/0094773 A1 | 4/2011 | Bare et al. |
| 2011/0144490 A1 | 6/2011 | Davis et al. |
| 2011/0152987 A1 | 6/2011 | Wahlgren et al. |
| 2011/0237922 A1 | 9/2011 | Parker, III et al. |
| 2011/0263490 A1 | 10/2011 | Kaplan et al. |
| 2011/0270360 A1 | 11/2011 | Harris et al. |
| 2012/0165792 A1 | 6/2012 | Ortiz et al. |
| 2012/0172783 A1 | 7/2012 | Harris et al. |
| 2012/0290023 A1 | 11/2012 | Boyden et al. |
| 2013/0110220 A1 | 5/2013 | Brown |
| 2014/0018767 A1 | 1/2014 | Harris et al. |
| 2014/0088487 A1 | 3/2014 | Harris et al. |
| 2014/0199278 A1 | 7/2014 | Kaplan et al. |
| 2015/0258326 A1 | 9/2015 | Harris et al. |
| 2016/0184574 A1 | 6/2016 | Harris et al. |
| 2018/0361138 A1 | 12/2018 | Harris et al. |
| 2019/0091464 A1 | 3/2019 | Harris et al. |
| 2019/0329023 A1 | 10/2019 | Harris et al. |

FOREIGN PATENT DOCUMENTS

| | | |
|---|---|---|
| CN | 2899835 Y | 5/2007 |
| EP | 1060728 A1 | 12/2000 |
| EP | 1172113 A1 | 1/2002 |
| JP | 2001259047 A | 9/2001 |
| JP | 2005021940 A | 1/2005 |
| JP | 2013126486 A | 6/2013 |
| WO | WO-1989011701 A1 | 11/1989 |
| WO | WO-1991000730 A1 | 1/1991 |
| WO | WO-199322277 A1 | 11/1993 |
| WO | WO-199506411 A1 | 3/1995 |
| WO | WO-199814200 A1 | 4/1998 |
| WO | WO-199845313 A1 | 10/1998 |
| WO | WO-199856397 A1 | 12/1998 |
| WO | WO-199900123 A1 | 1/1999 |
| WO | WO-200155109 A1 | 8/2001 |
| WO | WO-200170337 A1 | 9/2001 |
| WO | WO-200170708 A1 | 9/2001 |
| WO | WO-200215909 A1 | 2/2002 |
| WO | WO-2002012887 A2 | 2/2002 |
| WO | WO-2002018327 A2 | 3/2002 |
| WO | WO-2002059095 A1 | 8/2002 |
| WO | WO-2002059107 A1 | 8/2002 |
| WO | WO-2002059108 A1 | 8/2002 |
| WO | WO-2002059117 A1 | 8/2002 |
| WO | WO-2002067869 A2 | 9/2002 |
| WO | WO-2002068387 A2 | 9/2002 |
| WO | WO-2002068388 A2 | 9/2002 |
| WO | WO-2002081443 A1 | 10/2002 |
| WO | WO-2002085925 A2 | 10/2002 |
| WO | WO-2003006620 A2 | 1/2003 |
| WO | WO-2003007949 A1 | 1/2003 |
| WO | WO-2003009847 A1 | 2/2003 |
| WO | WO-2003009850 A1 | 2/2003 |
| WO | WO-2003026576 A2 | 4/2003 |
| WO | WO-2004078716 A1 | 9/2004 |
| WO | WO-2004078717 A1 | 9/2004 |
| WO | WO-2004087159 A1 | 10/2004 |
| WO | WO-2005033254 A1 | 4/2005 |
| WO | WO-2005040109 A1 | 5/2005 |
| WO | WO-2005047251 A1 | 5/2005 |
| WO | WO-2005077935 A1 | 8/2005 |
| WO | WO-2006019787 A2 | 2/2006 |
| WO | WO-2006020277 A2 | 2/2006 |
| WO | WO-2006072393 A2 | 7/2006 |
| WO | WO-2007015157 A2 | 2/2007 |
| WO | WO-2007015162 A1 | 2/2007 |
| WO | WO-2007041052 A2 | 4/2007 |
| WO | WO-2007041061 A2 | 4/2007 |
| WO | WO-2007047496 A2 | 4/2007 |
| WO | WO-2008063330 A2 | 5/2008 |
| WO | WO-2008087190 A2 | 7/2008 |
| WO | WO-2009008991 A2 | 1/2009 |
| WO | WO-2009067501 A2 | 5/2009 |
| WO | WO-2009097542 A2 | 8/2009 |
| WO | WO-2009117415 A2 | 9/2009 |
| WO | WO-2013115756 A2 | 8/2013 |

OTHER PUBLICATIONS

"3M CoTran™ 9705 Membrane" Brochure. (2009).
"3M CoTran™ 9706 Membrane" Brochure. (2009).
"3M CoTran™ 9707 Membrane" Brochure. (2009).
"3M CoTran™ 9712 Membrane" Brochure. (2009).
"3M CoTran™ 9715 Membrane" Brochure. (2009).
"3M CoTran™ 9716 Membrane" Brochure. (2009).
"3M CoTran™ 9728 Membrane" Brochure. (2009).
"3M CoTran™ Membranes" Brochure. (2010).
"Autonomic and Motor Nervous System." *Notes for Principles of Human Physiology*. Chapter 11. Retrieved 2014.
"Cell Junctions, Cell Adhesions, and the Extracellular Matrix." *Molecular Biology of the Cell*. Alberts et al., eds. New York: Garland Publishing. Chapter 19(1994):949-1009.
"PNS Platform and Therapies." *SPR Therapeutics*. Web. Aug. 23, 2014.
"Shining a Light on Disease—Tracking Light-Emitting Bacteria During Infection." *Soc. Gen. Microbiol.* (2009).
Accornero et al. "Selective Activation of Peripheral Nerve Fibre Groups of Different Diameter by Triangular Shaped Simulus Pulses." *J. Physiol.* 273(1977):539-560.
*Adenovirus Methods and Protocols*. Wold, ed. New Jersey: Humana Press. (1998).
Australian Office Action for Application No. 1010343059, dated Aug. 30, 2013 (5pages).
Ausubel et al. "Preparation of a Specific Retrovirus Producer Cell Line." *Current Protocols in Molecular Biology*. New York: Wiley & Sons. (1989):9.10-9.14.
Bakshi et al. "1-Amino-1,2,3,4-tetrahydronaphthalene-2-carboxylic Acid as a Tic Mimetics: Application in the Synthesis of Potent Human Melanocortin-4 Receptor Selective Agonists." *Bioorg. Med. Chem. Lett.* 15.14(2005):3430-3433.
Bartelet et al. "Brown Adipose Tissue Activity Controls Trigylceride Clearance." *Nat. Med.* 17.2(2011):200-206.
Bartelet et al. "The Holy Grail of Metabolic Disease: Brown Adipose Tissue." *Curr. Opin. Lipidol.* 23.3(2012):190-195.
Bartness et al 'Brain-Adipose Tissue Neural Crosstalk' Physiol Behav 91.4 (2007) pp. 343-351.
Bartness et al 'Sympathetic and Sensory Innervation of Brown Adipose Tissue' Int J Obes (Lond) 34(2010) pp. S36-S42.
Bartness et al 'Sympathetic and Sensory Innervation of White Adipose Tissue' J. Lipid Res 48(2007) pp. 1655-1672.
*Basic Methods in Molecular Biology*. Davis et al., eds. New York: Elsevier. (1986).
Berkner. "Development of Adenovirus Vectors for the Expression of Heterologous Genes." *Biotechniques*. 6.7(1988):616-629.
Bing et al. "Hyperphagia in Cold-Exposed Rats is Accompanied by Decreased Plasma Leptin but Unchanged Hypothamalic NPY." *Am. J. Physiol. Regul. Integ. Comp. Physiol.* 274(1998):62-68.
Birks. "Regulation by Patterned Preganglionic Neural Activity of Transmitter Stores in a Sympathetic Ganglion." *J. Physiol.* 28091978):559-572.

(56) References Cited

OTHER PUBLICATIONS

Boshart et al. "A Very Strong Enhancer is Located Upstream of an Immediate Early Gene of Human Cytomegalovirus." *Cell.* 41.2(1985):521-530.
Bostock et al. "Velocity Recovery Cycles of C Fibres Innervating Human Skin." *J. Physiol.* 553.2(2003):649-663.
Bouillaud et al. "Increased Level of mRNA for the Uncoupling Protein in Brown Adipose Tissue of Rats during Thermogenesis Induced by Cold Exposure or Norepinephrine Infusion." *J. Biol. Chem.* 259.18(1984):11583-11586.
Bredenbeek et al. "Sindbis Virus Expression Vectors: Packaging of RNA Replicons by Using Defective Helper RNAs." *J. Virol.* 67.11 (1993).
Bugajski et al. "Effect of Long-Term Vagal Simulation on Food Intake and Body Weight During Diet Induced Obesity in Rats." *J. Phys. Pharm.* 58(2007):5-12.
Cannon et al. "Brown Adipose Tissue: Function and Physiological Significance." *Physiol. Rev.* 84(2004):277-359.
Cannon et al. "Nonshivering Thermogenesis and its Adequate Measurement in Metabolic Studies." *J. Exp. Biol.* 214(2011):242-253.
Capecchi. "High Efficiency Transformation by Direct Microinjection of DNA into Cultured Mammalian Cells." *Cell.* 22(1980):479-488.
Cassiede et al. "Osteochondrogenic Potential of Marrow Mesenchymal Progenitor Cells Exposed to TGF-β 1 or PDGF-BB as Assayed In Vivo and In Vitro." *J. Bone Miner. Res.* 11.9(1996):1264-1273.
Cheneval et al. "Cell-Free Transcription Directed b the 422 Adipose P2 Gene Promoter: Activation by the CCAAT/Enhancer Binding Protein." *PNAS.* 88.19(1991):8465-8469.
Chu et al. "SV40 DNA Transfection of Cells in Suspension: Analysis of Efficiency of Transcription and Translation of T-Antigen." *Gene.* 13.2(1981):197-202.
Clark et al. "Gene Transfer into the CNS Using Recombinant Adeno-Associated Virus: Analysis of Vector DNA Forms Resulting in Sustained Expression." *J. Drug Target.* 7.4(1999):269-283.
Collins. "The Cervical Sympathetic Nerves in Surgery of the Neck." *Otolaryngol Head Neck Surg.* 105(1991):544-555.
Crago et al. "The Choice of Pulse Duration for Chronic Electrical Stimulation via Surface, Nerve, and Intramuscular Electrodes." *Ann. Biomed. Eng.* 2(1974):252-264.
Davidson et al. "A Model System for in vivo Gene Transfer into the Central Nervous System Using an Adenoviral Vector." *Nat. Genet.* 3.3(1993):219-223.
Douglas et al. "A System for the Propagaton of Adenoviral Vectors with Genetically Modified Receptor Specificities." *Nat. Biotechnol.* 17.5(1999):470-475.
Drazen et al. "Peripheral Signals in the Control of Satiety and Hunger." *Curr. Opin. Clin. Nutr. Metab. Care.* 6.6(2003):621-629.
Dull et al. "A Third-Generation Lentivirus Vector with a Conditional Packaging System." *J. Virol.* 72.11(1998):8463-8471.
Ekblom et al. "Laminin Isoforms and Epithelial Development." *Ann. N.Y. Acad. Sci.* 857(1998):194-211.
Enerback, Sven, "The Origins of Brown Adipose Tissue," *New England Journal of Medicine,* vol. 360:2023-2023 (2009).
Feigner et al. "Lipofection: A Highly Efficient, Lipid-Mediated DNA-Transfection Procedure." *PNAS.* 84.21(1987):7413-7417.
Flaim et al. "Functional and Anatomical Characteristics of the Nerve-Brown Adipose Interation in the Rat." *Pflügers Arch.* 365(1976):9-14.
Foster et al. "Hetergeneity of the Sympathetic Innervation of Rat Interscapular Browrn Adipose Tissue via Intercostal Nerves." *Can. J. Physiol. Pharmacol.* 60.6(1982):747-754.
Freeman, P et al 'Brown Adipose Tissue Thermogensis Induced by Low Level Electrical Stimulation of Hypothalamus in rats' Brain Reaserach Bulletin (1987) Vpo. 18 pp. 7-11.
Frolov et al. "Alphavirus-Based Expression Vectors: Strategies and Applications." *PNAS.* 93.21(1996):11371-11377.
Fruhbeck et al. "BAT: A New Target for Human Obesity?" *Trends Pharmacol. Sci.* 30.8(2009):387-396.

Graham et al. "A New Technique for the Assay of Infectivity of Human Adenovirus 5 DNA." *Virology.* 52.2(1973):456-467.
Grill et al Effect of Stimulus Pulse Duration on Selectivity of Neural Stimulation IEEE Trans Biomed Eng. 43.2 (1996) pp. 161-166.
Grill et al 'Stimulus Waveforms for Selective Neural Stimulation' IEEE Eng Med Biol (1995) pp. 375-385.
Gronthos et al. "The STRO-1+ Fraction of Adult Human Bone Marrow Contains the Osteogenic Precursors." *Blood.* 84.12(1994):4164-4173.
Heaton. "The Distribution of Brown Adipose Tissue in the Human." *J. Anat.* 112(1972):35-39.
Herlitze et al. "New Optical Tools for Controlling Neuronal Activity." *Curr. Opin. Neurobiol.* 17.1(2007):87-94.
Herpin et al. "Discovery of Tyrosine-Based Potent and Selective Melanocortin-1 Receptor Small-Molecule Agonists with Anti-Inflammatory Properties." *J. Med. Chem.* 46.7(2003):1123-1126.
Himms-Hagen et al 'Brown adipose tissue thermogenesis: Interdisciplinary Studies' FASEB J 4(1990) pp. 2894-2898.
Hodgkin et al. "A Quantitative Description of Membrane Current and its Application to Conduction and Excitation in Nerve." *J. Physiol.* 117(1952):500-544.
Horwitz et al. "Norepinephrine-Induced Depolarization of Brown Fat Cells." *PNAS.* 64(1969):113-120.
International Preliminary Report on Patentability dated Aug. 2, 2012 for Application No. PCT/US2010/062464 (6 Pages).
International Preliminary Report on Patentability dated Jul. 4, 2017 for Application No. PCT/US2015/065513 (7 pages).
International Preliminary Report on Patentability dated Jul. 4, 2017 for Application No. PCT/US2015/065516 (7 pages).
International Search Report and Written Opinion for Application No. PCT/US2015/065516 dated Apr. 7, 2016.
International Search Report and Written Opinion for PCT/US10/62464 dated Feb. 24, 2011 (8 pages).
International Search Report re: PCT/US2015/065513 dated Mar. 9, 2016 (6 pages).
Jaiswal et al. "Osteogenic Differentiation of Purified, Culture-Expanded Human Mesenchymal Stem Cells In Vitro." *J. Cell. Biochem.* 64.2(1997):295-312.
Johnstone et al. "In Vitro Chondrogenesis of Bone Marrow-Derived Mesenchymal Progenitor Cells." *Exp. Cell. Res.* 238.1(1998):265-272.
Kafri et al. "A Packaging Cell Line for Lentivirus Vectors." *J. Virol.* 73.1(1999):576-584.
Klein et al. "High-Velocity Microprojectiles for Delivering Nucleic Acids into Living Cells." *Nature.* 327(19897):70-73.
Ladner et al. "Human CSF-1: Gene Structure and Alternative Splicing of mRNA Precursors." *EMBO J.* 6.9(1987):2693-2698.
Lever et al. "Demonstration of a Catecholaminergic Innervation in Human Perirenal Brown Adipose Tissue at Various Ages in the Adult." *Anat. Rec.* 215.3(1986):251-5, 227-229.
Lin et al. "Spatially Discrete, Light Driven Protein Expression." *Chem. Biol.* 9(2002):1347-1353.
Makino et al. "Cardiomyocytes can be Generated from Marrow Stromal Cells in vitro." *J. Clin. Invest.* 103.5(1999):697-705.
Mannino et al. "Liposome Mediated Gene Transfer." *Biotech.* 6.7(1988):682-690.
Masamoto et al. "Intragastric Administration of TRPV1, TRPV3, TRPM8, and TRPA1 Agonists Modulates Autonomic Thermoregulation in Different Manners in Mice." *Biosci. Biotechnol. Biochem.* 73.5(2009):1021-127.
Mayer et al. "Biologically Active Molecules with a 'Light Switch.'" *Angew. Chem. Int. Ed.* 45(2006):4900-4921.
McKnight et al. "The Distral Transcription Signals of the Herpesvirus tk Gene Share a Common Hexanucleotide Control Sequence." *Cell.* 37.1(1984):253-262.
McMinn et al. "Neuroendocrine Mechanisms Regulating Food Intake and Body Weight." *Obes. Rev.* 1.1(2000):37-46.
Minokoshi et al. "Sympathetic Acticatioon of Lipid Synthesis in Brown Adipose Tissue in the Rat." *J. Physiol.* 398(1988):361-370.
Mochizuki et al. "High-Titer Human Immunodeficiency Virus Type 1-Based Vector Systems for Gene Delivery into Nondividing Cells." *J. Virol.* 72.11(1998):8873-8883.

(56) References Cited

OTHER PUBLICATIONS

Molecular Biology of the Cell, 3rd Edition, ed. by Alberts et al., New York: Garland Publishing, 1994, Ch. 19.
*Molecular Cloning.* Sambrook et al., eds.New York: Cold Spring Harbor Laboratories. (1989).
Morrison et al 'Central Control of Brown Adipose Tissue Thermogenesis' Front. Endocrinol. 3(2012) pp. 1-19.
Morrison, S.F. RVLM and raphe differentially regulate sympathetic outflows to splanchnic and brown adipose tissue, American Journal of Physiology—Regulatory, Integrative and Comparative Physiology, published Apr. 1, 1999, vol. 276 No. 4 pp. 962-973.
National Institute of Health. "Clinical Guidelines on the Idenfication, Evaluation, and Treatment of Overweight and Obesity in Adults." (1998).
Ng et al. "Evolution of the Functional Human β-Actin Gene and its Multi-Pseudogene Family: Conservation of Noncoding Regions and Chromosomal Dispersion of Pseudogenes." *Mol. Cell Biol.* 5.10(1985):2720-2732.
Office action issued in Chinese Application No. 201080065678.8 dated Mar. 21, 2014. (Chinese original and English translation).
Office action issued in Japanese Application No. 2012-550003 dated Sep. 16, 2014. (Japanese original and English translation).
Palucki et al. "Discovery of (2S)-N-[(1R)-2-[4-cyclohexyl-4-[[(1,1-dimethylethyl)amino]carbonyl]-1-piperidinyl]-1-[(4-fluorophenyl)methyl]-2-oxoethyl]-4-methyl-2-piperazinecarboxamide (MB243), a Potent and Selective Melanocortin Subtype-4 Receptor Agonist."*Bioorg. Med. Chem. Lett.* 15.1(2005):171-175.
Rehnmark et al. "α- and β-Adrenergic Induction of the Expression of the Uncoupling Protein Thermogenin in Brown Adipocytes Differentiated in Culture." *J. Biol. Chem.* 265(1990):16464-16471.
Reiman et al. "Characterization and Functional Role of Voltage Gated Cation Conductances in the Glucagon-Like Peptide-1 Secreting GLUTag Cell Line." *J. Physiol.* 563(2005):161-171.
Rial et al. "The Structure and Function of the Brown Fat Uncoupling UCP1: Current Status." *Biofactors.* 8(1998):209-219.
Ricquier et al. "Contribution to the Identification and Analysis of the Mitochondrial Uncoupling Proteins." *J. Bioenergetics Biomembranes.* 31.5(1999):407-418.
Rosell et al. "Skin Impedance from 1Hz to 1MHz." *IEEE Trans. Biomed. Eng.* 35.8(1988):649-651.
Rosenfeld et al. "Adenovirus-Mediated Transfer of Recombinant α 1-Antitrypsin Gene to the Lung Epithelium in vivo." *Science.* 252(1991):431-434.
Rosenfeld et al. "In Vivo Transfer of the Human Cystic Fibrosis Transmembrane Conductance Regulator Gene to the Airway Epithelium." *Cell.* 68.1(1992):143-155.
Rothwell et al. "A Role for Brown Adipose Tissues in Diet-Induced Thermogenesis." *Nature.* 281(1979):31-35.
Saito et al. "High Incidence of Metabolically Active Brown Adipose Tissue in Healthy Adult Humans: Effects of Cold Exposure and Adisposity." *Diabetes.* 58(2009):1526-1531.
Salmons et al. "Targeting of Retroviral Vectors for Gene Therapy." *Hum. Gene Ther.* 4(1993):129-141.
Schmelz et al. "Delayed Responses to Electrical Stimuli Reflect C-Fiber Responsiveness in Human Microneurography." *Exp. Brain Res.* 104(1995):331-336.
Sebhat et al. "Design and pharmacology of N-[(3R)-1,2,3,4-tetrahydroisoquinolinium- 3-ylcarbonyl]-(1R)-1-(4-chlorobenzyl)-2-[4-cyclohexyl-4-(1H-1,2,4-triazol-1-ylmethyl)piperidin-1-yl]-2-oxoethylamine (1), a potent, selective, melanocortin subtype-4 receptor agonist." *J. Med. Chem.* 45.21(2002):4589-4593.
Seydoux et al. "Impaired Metabolic Response to Nerve Stimulation in Brown Adipose Tissue of Hypothyroid Rats." *Mol. Cell. Endocrinol.* 25(1982):213-226.
Shigekawa et al. "Electroporation of Eukaryotes and Prokaryotes: A General Approach to the Introduction of Macromolecules into Cells." *Biotechniques.* 6.8(1988):742-751.
Shimizu et al. "Sympathetic Activation of Glucose Utilization in Brown Adipose Tissue in Rats." *J. Biochem.* 110.5(1991):688-692.

Solicore Flexicon Batteries Product Line, available at Solicore, Inc. date of first publication unknown, revision 3 date Jan. 2007.
Solicore SF-2529 Product Brochure, date of first publication unknown, revision 2 dated Aug. 2008.
Solicore SF-4823 Product Brochure, date of first publication unknown, revision 2 dated Aug. 2008.
Stylopoulos et al. "Roux-en-Y Gastric Bypass Enhances Energy Expenditure and Extends Lifespan in Diet-Induced Obese Rats." *Obesity.* 17(2009):1839-1847.
Supplementary European Search Report re: EP10844295 dated Aug. 1, 2013.
*Sustained and Controlled Release Drug Delivery Systems.* Robinson, ed. New York: Marcel Dekker. (1978).
Sutton et al. "Human Immunodeficiency Virus Type 1 Vectors Efficiently Transduce Human Hematopoietic Stem Cells." *J. Virol.* 72.7(1998):5781-5788.
Tajino et al. "Application of Menthol to the Skin of Whole Trunk in Mice Induces Autonomic and Behavorial Heat-Gain Responses." *Am. J. Physiol. Regul. Integr. Comp. Physiol.* 293.5(2007):R2128-2135.
Testerman et al. "Electrical Stimulation as Therapy for Neurological Disorders: The Basics of Implantable Neurological Stimulators." *IEEE Eng. Med. Biol. Mag.* (2006):74-78.
Toii et al. "Fall in Skin Temperature of Exercising Man." *Br. J. Sp. Med.* 26.1(1992):29-32.
U.S. Appl. No. 13/977,555, filed Jun. 28, 2013.
U.S. Appl. No. 14/584,046, filed Dec. 29, 2014.
U.S. Appl. No. 61/427,968, filed Dec. 29, 2010.
U.S. Appl. No. 61/427,991, filed Dec. 29, 2010.
U.S. Appl. No. 61/428,008, filed Dec. 29, 2010.
U.S. Appl. No. 61/428,013, filed Dec. 29, 2010.
van Marken Lichtenbelt et al. "Cold Activated Brown Adipose Tissue in Healthy Men." *N. Eng. J. Med.* 360(2009):1500-1508.
Virtanen et al. "Functional Brown Adipose Tissue in Healthy Adults." *N. Eng. J. Med.* 360.15(2009):1518-1525.
Wagner et al. "Coupling of Adenovirus to Transferrin-Polylysine/DNA Complexes Greatly Enhances Receptor-Mediated Gene Delivery and Expression of Transfected Genes." *PNAS.* 89.13(1992):6099-6103.
Weidner et al. "Time Course of Post-Excitatory Effects Separates Afferent Human C Fibre Classes." *J. Physiol.* 527(2000):185-191.
Wells et al. "Application of Infrared Light for in vivo Neural Stimulation." *J. Biomed. Opt.* 10.6(2005):064003.
Wells et al. "Biophysical Mechanisms of Transient Optical Stimulation of Peripheral Nerve." *Biophys. J.* 93.7(2007):2567-2580.
Wells et al. "Optical Stimulation of Neural Tissue in vivo." *Opt. Lett.* 30.5(2005):504-506.
Wells et al. "Optically Mediated Nerve Stimulation: Identification of Injury Thresholds." *Lasers Surg. Med.* 39.6(2007):513-526.
Wells et al. "Pulsed Laser Versus Electrical Energy for Peripheral Nerve Stimulation." *J. Neurosci. Meth.* 163.2(2007):326-337.
Wold, W. Adenovirus Methods and Protocols, Humana Methods in Molecular Medicine (1998) Blacwell Science Ltd.
Wu et al. "A Pilot Study to Evaluate the Effect of Splanchnic Nerve Stimulation on Body Composition and Food Intake in Rats." *Obes. Surg.* 19(2009):1581-1585.
Xiong et al. "Sindbis Virus: AN Efficient, Broad Host Range Vector for Gene Expression in Animal Cells." *Science.* 243(1989):1188-1191.
Xu et al. "CMV-β-Actin Promoter Directs Higher Expression from an Adeno-Associated Viral Vector in the Liver than the Cytomegalovirus or Elongation Factor 1α Promoter and Results in Therapeutic Levels of Human Factor X in Mice." *Hum. Gene Ther.* 12.5(2001):563-573.
Ye et al. "Discovery and Activity of (1R, 4S, 64)-N-[(1R)-2-[4-cyclohexyl-4-[[(1,1-dimethylethyl0amino]carbonyl]-1-piperidinyl]-1-[(4-fluorophenyl)methyl]-2-oxoethyl]-2-methyl-2-azabicycylo[2.2.2]octane-6-carboxamide (3,RY764), a Potent and Selective Melanocortin Subtype-4 Receptor Agonist." *Bioorg. Med. Chem. Lett.* 15. 15(2005):3501-3505.
Yin et al. "Inhibitory Effects of Intestinal Electrical Stimulation on Food Intake, Weight Loss, and Gastric Emptying in Rats." *Am. J. Physiol. Regul. Integr. Comp. Physiol.* 293.1(2007):R78-R82.

(56) References Cited

OTHER PUBLICATIONS

Yoo et al. "The Condrogenic Potential of Human Bone-Marrow-Derived Mesenchymal Progenitor Cells." *J. Bone Joint Surg. Am.* 80.12(1998):1745-1757.

Zhao et al. "A Novel Promoter Controls Cyp19a1 Gene Expression in Mouse Adipose Tissue." *Reprod. Biol. Endocrinol.* 7(2009):37.

Zheng et al. "Stimulation of Sympathetic Innervations in the Upper Gastrointestinal Tract as a Treatment for Obesity." *Med. Hyp.* 72(2009):706-710.

METHODS AND DEVICES FOR ACTIVATING BROWN ADIPOSE TISSUE USING ELECTRICAL ENERGY

CROSS-REFERENCE TO RELATED APPLICATIONS

The present application claims priority to U.S. patent application Ser. No. 16/445,725 entitled "Methods And Devices For Activating Brown Adipose Tissue Using Electrical Energy" filed Jun. 19, 2019, which claims priority to U.S. patent application Ser. No. 16/197,786 entitled "Methods And Devices For Activating Brown Adipose Tissue Using Electrical Energy" (now U.S. Pat. No. 10,391,298) filed Nov. 21, 2018, which claims priority to U.S. patent application Ser. No. 16/108,730 entitled "Methods And Devices For Activating Brown Adipose Tissue Using Electrical Energy" (now U.S. Pat. No. 10,207,102) filed Aug. 22, 2018, which claims priority to U.S. patent application Ser. No. 14/584,066 entitled "Methods And Devices For Activating Brown Adipose Tissue Using Electrical Energy" (now U.S. Pat. No. 10,080,884) filed Dec. 29, 2014, which are hereby incorporated by reference in their entireties.

FIELD OF THE INVENTION

The present invention relates to methods and devices for activating brown adipose tissue using electrical energy.

BACKGROUND OF THE INVENTION

Obesity is becoming a growing concern, particularly in the United States, as the number of people with obesity continues to increase and more is learned about the negative health effects of obesity. Severe obesity, in which a person is 100 pounds or more over ideal body weight, in particular poses significant risks for severe health problems. Accordingly, a great deal of attention is being focused on treating obese patients.

Surgical procedures to treat severe obesity have included various forms of gastric and intestinal bypasses (stomach stapling), biliopancreatic diversion, adjustable gastric banding, vertical banded gastroplasty, gastric plications, and sleeve gastrectomies (removal of all or a portion of the stomach). Such surgical procedures have increasingly been performed laparoscopically. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall. However, such surgical procedures risk a variety of complications during surgery, pose undesirable post-operative consequences such as pain and cosmetic scarring, and often require lengthy periods of patient recovery. Patients with obesity thus rarely seek or accept surgical intervention, with only about 1% of patients with obesity being surgically treated for this disorder. Furthermore, even if successfully performed and initial weight loss occurs, surgical intervention to treat obesity may not result in lasting weight loss, thereby indicating a patient's need for additional, different obesity treatment.

Nonsurgical procedures for treating obesity have also been developed. However, effective therapies for increasing energy expenditure and/or altering a patient's metabolism, e.g., a basal metabolic rate, leading to improvements in metabolic outcomes, e.g., weight loss, have focused on pharmaceutical approaches, which have various technical and physiological limitations.

It has been recognized in, for example, U.S. Pat. No. 6,645,229 filed Dec. 20, 2000 and entitled "Slimming Device," that brown adipose tissue (BAT) plays a role in the regulation of energy expenditure and that stimulating BAT can result in patient slimming. BAT activation is regulated by the sympathetic nervous system and other physiological, e.g., hormonal and metabolic, influences. When activated, BAT removes free fatty acids (FFA) and oxygen from the blood supply for the generation of heat. The oxidative phosphorylation cycle that occurs in the mitochondria of activated BAT is shown in FIGS. 1 and 2.

Accordingly, there is a need for improved methods and devices for treating obesity and in particular for activating BAT.

SUMMARY OF THE INVENTION

The present invention generally provides methods and devices for activating brown adipose tissue using electrical energy. In one embodiment, a medical method is provided that includes positioning a device in contact with tissue of a patient proximate to a depot of BAT, and activating the device to transcutaneously deliver an electrical signal to the patient so as to activate a first nerve type in the BAT without activating a second, different nerve type in the BAT. The first nerve type can have a smaller diameter than the second nerve type. The electrical signal can have a peak current that is at least about 50 mA.

The method can vary in any number of ways. For example, the first nerve type can include sympathetic nerves, and the second nerve type can include parasympathetic nerves. For another example, the first nerve type can include sympathetic nerves, and the second nerve type can include sensory nerves. For yet another example, the electrical signal can have a peak current in a range of about 50 mA to 100 mA. For another example, the electrical signal can have a current of at least 10 mA. For still another example, the electrical signal can have a pulse width less than about 400 µs. For another example, the electrical signal is continuously delivered to the patient for at least one day. For still another example, positioning the device can include positioning at least a partial portion of the device external to the patient, and the method can include, after the delivering of the electrical signal so as to activate the first nerve type in the BAT, removing the device from being in contact with the tissue of the patient, repositioning the device in contact with tissue of the patient proximate to a different depot of BAT, and activating the device to deliver a second electrical signal to the patient so as to activate the first nerve type in the different depot of BAT without activating a second, different nerve type in the different depot of BAT.

In another embodiment, a medical method is provided that includes positioning a device in contact with tissue of a patient proximate to a depot of BAT, and activating the device to deliver an electrical signal to the patient so as to activate unmyelinated neurons in the BAT without activating myelinated neurons in the BAT. The electrical signal can have a current of at least 10 mA.

The method can have any number of variations. For example, the myelinated neurons can have a diameter in a range of about 2 µm to 6 µm. For another example, a peak current of the electrical signal can be in a range of about 50 mA to 100 mA. For yet another example, the electrical signal can have a pulse width less than about 400 µs. For another example, positioning the device can include transcutaneously applying the device to an exterior skin surface of the patient. For yet another example, positioning the device can include subcutaneously positioning a partial portion of the device within the patient. For still another example, positioning the device can include implanting the device entirely within the patient. For another example, the device is in continuous direct contact with the tissue of the patient for at least one day with the device continuously delivering the electrical signal to the patient for the at least one day.

In another aspect, a medical apparatus is provided that in one embodiment includes at least one electrode configured to directly contact a tissue of a patient proximate to a depot of BAT and to deliver an electrical signal to the patient so as to activate a first nerve type in the BAT without activating a second, different nerve type in the BAT. The first nerve type can have a smaller diameter than the second nerve type. The apparatus can also include at least one signal generator in electronic communication with the at least one electrode and configured to generate the electrical signal delivered by the at least one electrode.

The apparatus can have any number of variations. For example, an entirety of the apparatus can be configured to be implanted within the patient with the at least one electrode directly contacting at least one of the depot of BAT, the first nerve type, and the second nerve type. For another example, only a partial portion of the apparatus can be configured to be implanted within the patient. For yet another example, the at least one electrode can be configured to be positioned entirely external to the patient and be positioned on a skin surface of the patient.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
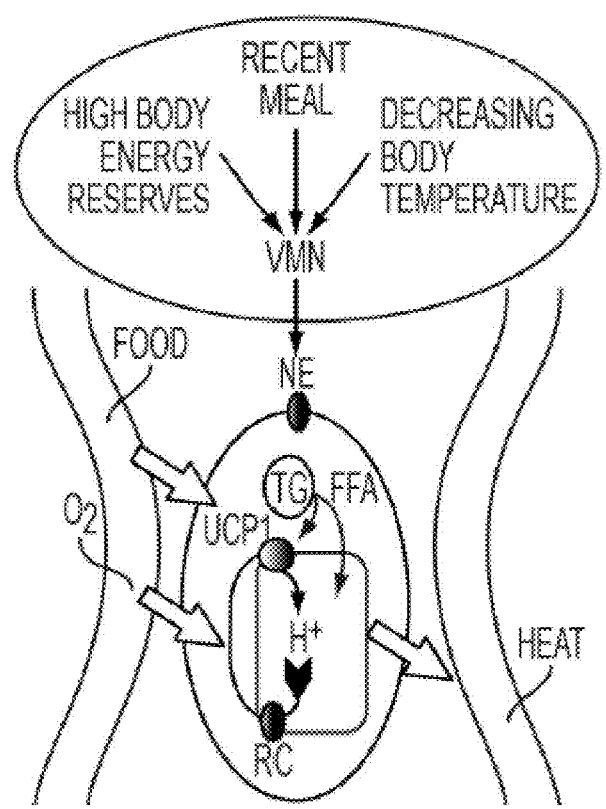
FIG. 1 is a schematic view of an oxidative phosphorylation cycle that occurs in mitochondria within BAT cells.
Figure 2:
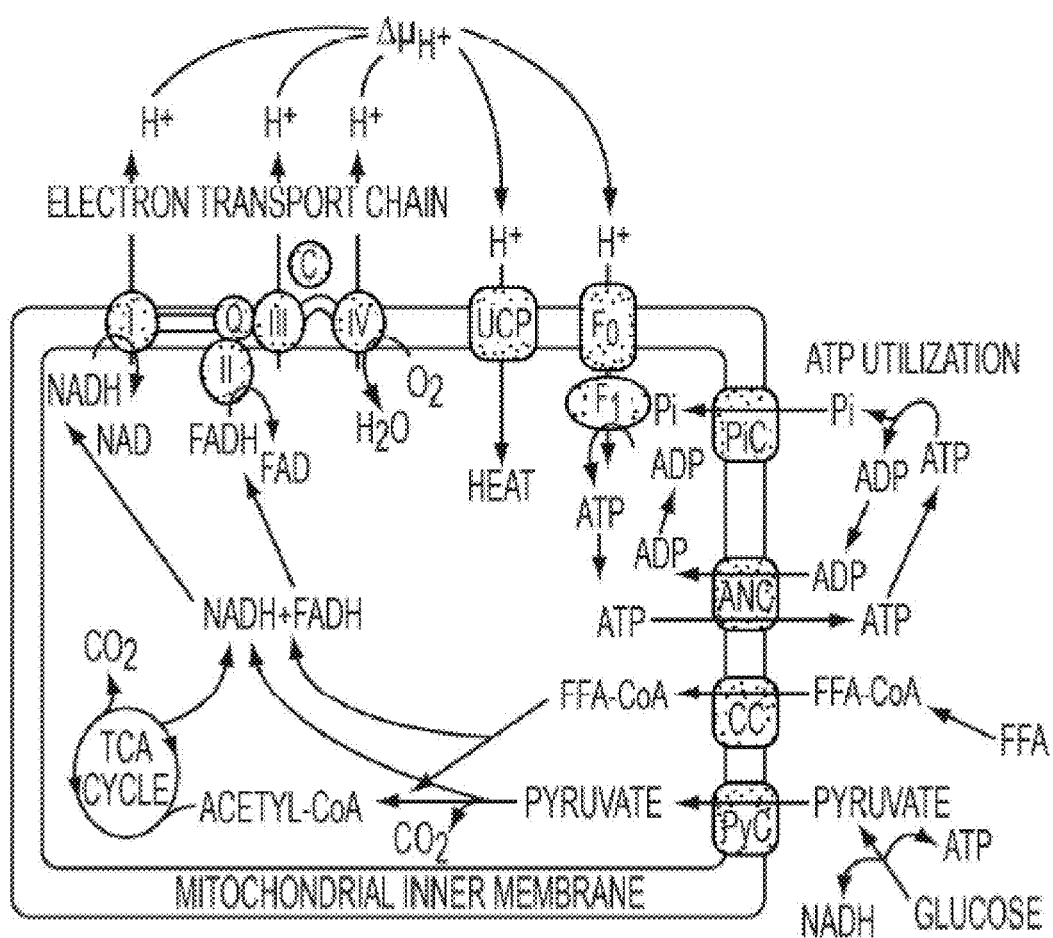
FIG. 2 is a schematic view of BAT mitochondria showing an oxidative phosphorylation cycle that occurs in the mitochondria.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Methods and Devices

Various exemplary methods and devices are provided for activating brown adipose tissue (BAT) using electrical energy. In general, the methods and devices can facilitate activation of BAT to increase thermogenesis, e.g., increase heat production and energy expenditure in the patient, which over time can lead to one or more of weight loss, a change in the metabolism of the patient, e.g., increasing the patient's basal metabolic rate, and improvement of comorbidities associated with obesity, e.g., Type II diabetes, high blood pressure, etc. In an exemplary embodiment, a medical device is provided that activates BAT by electrically stimulating nerves that activate the BAT and/or electrically stimulating brown adipocytes directly, thereby increasing thermogenesis in the BAT and inducing weight loss, increasing metabolic rate, and/or improving one or more comorbidities through energy expenditure. In this way, weight loss, increased metabolic rate, and/or comorbidity improvement can be induced without performing a major surgical procedure, without relying on administration of one or more pharmaceuticals, without relying on cooling of the patient, and without surgically altering a patient's stomach and/or other digestive organs.

The electrical energy applied to BAT can include an electrical signal configured to target sympathetic nerves that can directly innervate BAT. The electrical signal can be configured to target the sympathetic nerves using fiber diameter selectivity. In other words, the electrical signal can be configured to activate nerve fibers having a first diameter without activating nerve fibers having diameters different than the first diameter. Sympathetic nerves include postganglionic unmyelinated, small diameter fibers, while parasympathetic nerves that can directly innervate BAT include preganglionic myelinated, larger diameter fibers. The electrical signal can be configured to target and activate the postganglionic unmyelinated, small diameter fibers without activating the preganglionic myelinated, larger diameter fibers. The energy required to activate the postganglionic unmyelinated, small diameter fibers (e.g., the sympathetic nerves) is greater than the energy required to activate the preganglionic myelinated, larger diameter fibers (e.g., the parasympathetic nerves). The energy of the electrical signal can be relatively high so as to activate the sympathetic fibers without activating the parasympathetic nerves. The electrical signal can thus effectively activate the BAT because, as will be appreciated by a person skilled in the art, stimulating the sympathetic nervous system that includes sympathetic nerves can effectively activate BAT.

The electrical signal applied to BAT that is configured to target sympathetic nerves can include a simple signal including a single wave (e.g., a square wave, etc.), or the electrical signal applied to BAT that is configured to target sympathetic nerves can include a plurality of waves (e.g., a carrier signal and a modulating signal). Embodiments of electrical signals to activate BAT are discussed further below and are described in U.S. Pat. Pub. No. 2011/0270360 entitled "Methods And Devices For Activating Brown Adipose Tissue Using Electrical Energy" filed Dec. 29, 2010, which is hereby incorporated by reference in its entirety.

The diameter of sympathetic nerve fibers can be about 2 μm. A person skilled in the art will appreciate that the diameter of a sympathetic nerve fiber may not be precisely 2 μm but nevertheless be considered to be 2 μm due to one or more factors, such as precision of instruments used to measure fiber diameters. Sympathetic nerve fibers that branch forming small diameter axon with intermittent varicosities can have a diameter that is less than 2 μm. The electrical signal applied to BAT can thus be configured to target nerve fibers having a diameter of about 2 μm or less.

Parasympathetic and sympathetic nerves form an efferent pathway including preganglionic and postganglionic neurons. Second-order postganglionic neurons synapse on smooth and cardiac muscle and also control glandular secretion. In addition to preganglionic and postganglionic neurons, control systems of the autonomic nervous system (ANS) that includes the sympathetic and parasympathetic nervous systems also involve supraspinal controlling and integrative neuronal centers; supraspinal, spinal, ganglionic, and peripheral interneurons; and afferent neurons. Afferent neurons have cell bodies in the dorsal root ganglia or cranial nerve somatic sensory ganglia. Afferent axons travel in somatic peripheral nerves or along with autonomic efferent nerves.

The parasympathetic preganglionic component of the ANS has a supraspinal and spinal portion. Parasympathetic preganglionic neurons are found in four parasympathetic brain stem nuclei: nucleus Edinger-Westphal, superior salivatory nucleus, inferior salivatory nucleus, and the dorsal vagal complex of the medulla. Their axons exit via cranial nerves 3 (oculomotor); 7 (facial nerve); 9 (glossopharyngeal nerve); and 10 (vagus nerve) respectively. Parasympathetic preganglionic neurons are also found in the intermediolateral (IML) cell column of the sacral spinal cord in segments S2-S4 and exit the central nervous system (CNS) via the sacral ventral roots and the spinal nerves and then continue to the pelvic viscera as the pelvic nerve. The sacral preganglionic parasympathetic efferent axons of the pelvic nerve synapse with postganglionic parasympathetic neurons in the ganglia of the pelvic plexus. Postganglionic axons innervate the descending colon, rectum, urinary bladder, and sexual organs.

The sympathetic preganglionic component of the ANS is purely spinal. Sympathetic preganglionic neurons (SPNs) are found in the IML cell column of the thoracic and lumbar spinal cord in segments T1-L2 and exit the CNS via the thoracolumbar ventral roots. The sympathetic segmental outflow can vary, and the outflow can start as high as C8 or as low as T2 and end at L1 or L3. The thinly myelinated preganglionic fibers exit via the ventral roots as the white rami communicantes. Many sympathetic preganglionic fibers synapse in the paravertebral ganglia, which are paired and lie next to the spine from the cervical to the sacral segments. There are three cervical paravertebral ganglia: the superior cervical ganglion, the middle cervical ganglion, and the stellate ganglion. There are usually eleven thoracic ganglia, four lumbar ganglia, and four or five sacral ganglia. Sympathetic preganglionic axons can synapse in paravertebral ganglia at the segment of their exit or can pass up or down several segments of the sympathetic chain before synapsing. One sympathetic preganglionic axon will synapse with several postganglionic neurons. Postganglionic axons are unmyelinated, small diameter fibers that leave the paravertebral ganglia via the gray rami communicantes and exit via the segmental spinal nerves.

Some sympathetic preganglionic axons pass through the paravertebral ganglia without synapsing and constitute the splanchnic nerves that innervate three prevertebral ganglia: celiac ganglion, superior mesenteric ganglion, and inferior mesenteric ganglion (IMG), as well as the adrenal medulla. Postsynaptic axons from the prevertebral ganglia course to the abdominal and pelvic viscera as the hypogastric, splanchnic, and mesenteric plexuses.

Sweat glands, piloerector muscles, and most small blood vessels receive only sympathetic innervation. Diffuse sympathetic nervous system discharge results in pupillary dilatation, increased heart rate and contractility, bronchodilation, vasoconstriction of the mesenteric circulation, and vasodilation of skeletal muscle arterioles. This is the "fight or flight" defense reaction.

Supraspinal neurons involved in the control systems of the ANS are located in the nucleus of the tractus solitarius (NTS), nucleus ambiguus, dorsal motor nucleus of vagus, dorsal raphe nucleus, medullary reticular formation nuclei, locus ceruleus, hypothalamus, limbic system, and the primary sensory and motor cortex. The hypothalamus has uncrossed sympathetic descending pathways to the midbrain, lateral pons, and medullary reticular formation. Descending reticulospinal pathways from the pons and medulla to interneurons in the spinal cord influence the IML cells. The NTS receives afferents from the viscera and functions as an integrating center for reflex activity as well as a relay station to the hypothalamus and limbic systems.

At the effector organs, sympathetic ganglionic neurons release noradrenaline (norepinephrine), along with other cotransmitters such as adenosine triphosphate (ATP), to act on adrenergic receptors, with the exception of the sweat glands and the adrenal medulla. Acetylcholine is the preganglionic neurotransmitter for both divisions of the ANS, as well as the postganglionic neurotransmitter of parasympathetic neurons. Nerves that release acetylcholine are said to be cholinergic. In the parasympathetic system, ganglionic neurons use acetylcholine as a neurotransmitter, to stimulate muscarinic receptors. At the adrenal cortex, there is no postsynaptic neuron. Instead, the presynaptic neuron releases acetylcholine to act on nicotinic receptors. Stimulation of the adrenal medulla releases adrenaline (epinephrine) into the bloodstream which will act on adrenoceptors, producing a widespread increase in sympathetic activity.

Following a surgical procedure to treat obesity such as Roux-en-Y gastric bypass (RYGB), a patient can lose weight due to an increase in energy expenditure, as demonstrated in a rodent model for example in Stylopoulos et al., "Roux-en-Y Gastric Bypass Enhances Energy Expenditure And Extends Lifespan In Diet-Induced Obese Rats," *Obesity* 17 (1 Oct. 2009), 1839-47. Additional data from Stylopoulos et al. (not published in the previous article or elsewhere as of the filing date of the present application) indicates that RYGB is also associated with increased levels of uncoupling protein 1 (UCP1), which is an uncoupling protein in mitochondria of BAT, as well as with a significant reduction in the size of fat stores within BAT and an increased volume of BAT. It thus appears that RYGB causes activation of BAT, although as discussed above, surgical procedures to treat obesity, such as gastric bypass, risk if not necessarily cause a variety of undesirable results in at least some patients. Devices and methods to activate BAT without a major surgical procedure like RYGB but instead with electrical nerve stimulation to increase energy expenditure are therefore provided.

One characteristic of BAT that distinguishes it from white adipose tissue (WAT) stores is the high number of mitochondria in a single BAT cell. This characteristic makes BAT an excellent resource for burning energy. Another distinguishing characteristic of BAT is that when activated, UCP1 is utilized to introduce inefficiency into the process of adenosine triphosphate (ATP) creation that results in heat generation. Upregulation of UCP1 is therefore a marker of BAT activation.

Activation of brown adipocytes leads to mobilization of fat stores within these cells themselves. It also increases transport of FFA into these cells from the extracellular space and bloodstream, particularly when the local reserves that are associated with BAT are depleted. FFAs in the blood are derived primarily from fats metabolized and released from adipocytes in WAT as well as from ingested fats. Stimulation of the sympathetic nervous system is a major means of physiologically activating BAT. Sympathetic nerve stimulation also induces lipolysis in WAT and release of FFA from WAT into the bloodstream to maintain FFA levels. In this way, sympathetic stimulation leads ultimately to the transfer of lipids from WAT to BAT followed by oxidation of these lipids as part of the heat generating capacity of BAT. This activation of brown adipocytes can also lead to improvements in diabetes related markers.

Figure 3:
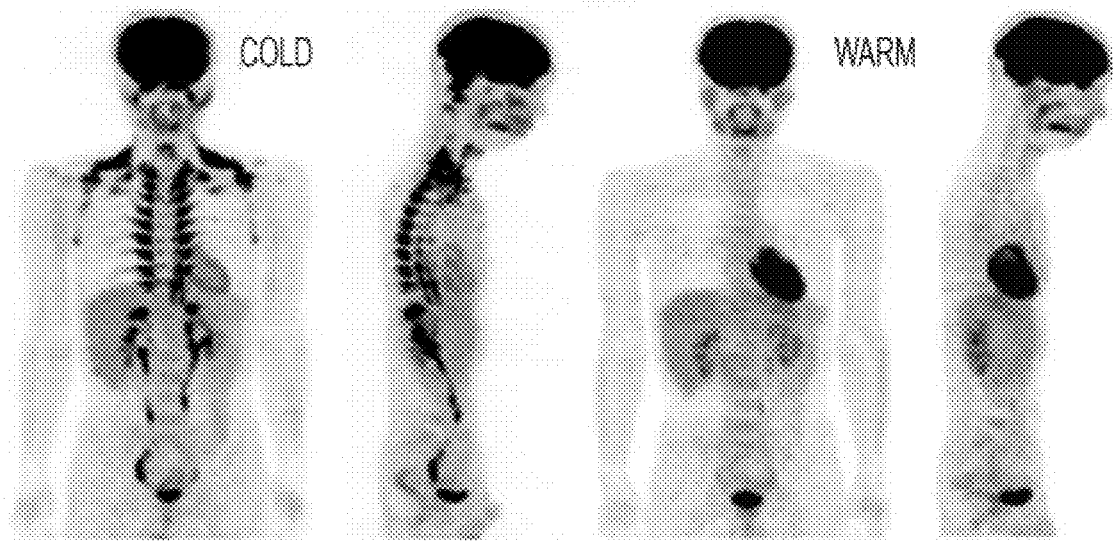
FIG. 3 is a schematic view of PET-CT images showing the locations of BAT depots in a patient subject to a cold environment and in the patient in a normal, warm environment.

The controlled activation of BAT can be optimized, leading to weight loss, increased metabolic rate, and/or comorbidity improvement, by reducing the stores of triglycerides in WAT. A person skilled in the art will appreciate that exposure to cold temperature leads to the activation of BAT to help regulate body temperature. This knowledge allows the location of BAT to be readily assessed using positron emission tomography-computed tomography (PET-CT) imaging. FIG. 3 shows scans of a patient subjected to a cold environment (left two images) and the same patient scanned in a normal, warm environment (right two images). Shown in black are regions of intense glucose uptake—namely, the brain, the heart, the bladder, and in the cold environment, BAT. However these images show the locations of BAT depots—namely the nape of the neck, the supraclavicular region, over the scapula, alongside the spinal cord, and around the kidneys as referenced by, for example, Rothwell et al, "A Role For Brown Adipose Tissue In Diet-Induced Thermogenesis," *Nature*, Vol. 281, 6 Sep. 1979, and Virtanen et al., "Functional Brown Adipose Tissue in Healthy Adults," *The New England Journal of Medicine*, Vol. 360, No. 15, Apr. 9, 2009, 1518-1525.

A person skilled in the art will appreciate that adult humans have substantial BAT depots, as indicated, for example, in J. M. Heaton, "The Distribution Of Brown Adipose Tissue In The Human," *J Anat.*, 1972 May, 112(Pt 1): 35-39, and W. D. van Marken Lichtenbelt et al, "Cold-Activated Brown Adipose Tissue in Healthy Men," N. Engl. J. Med., 2009 April, 360, 1500-1508. A person skilled in the art will also appreciate that BAT is heavily innervated by the sympathetic nervous system, as indicated, for example, in Lever et al., "Demonstration Of A Catecholaminergic Innervation In Human Perirenal Brown Adipose Tissue At Various Ages In The Adult," *Anat Rec.*, 1986 July, 215(3): 251-5, 227-9. Further, "[t]he thin unmyelinated fibers that contain norepinephrine (and not NPY) are those that actually innervate the brown adipocytes themselves. They form a dense network within the tissue, being in contact with each brown adipocyte (bouton-en-passant), and their release of norepinephrine acutely stimulates heat production and chronically leads to brown adipose tissue recruitment." B. Cannon, and J. Nedergaard, "Brown Adipose Tissue: Function And Physiological Significance," *Physiol Rev.*, 2004: 84: 277-359.

Sympathetic nerves innervating BAT can be neuromodulated to activate UCP1 and hence increase energy expenditure through heat dissipation through transcutaneous and/or direct neuromodulation of sympathetic nerves innervating BAT. Transcutaneous and direct neuromodulation are each discussed below in more detail.

In some embodiments, transcutaneous and/or direct neuromodulation of sympathetic nerves innervating BAT can be combined with one or more treatments, before and/or after transcutaneous and/or direct stimulation of BAT, which can help encourage BAT activation and/or increase an amount of BAT in a patient. One or more techniques to activate BAT can be used at a time, e.g., a patient can be cooled and electrically stimulated. For a non-limiting example of such a treatment, exposure to cold temperature can lead to the activation of BAT to help regulate body temperature. Exemplary embodiments of using cooling to activate BAT are described in U.S. application Ser. No. 13/977,555 entitled "Methods And Devices For Activating Brown Adipose Tissue With Cooling" filed Jun. 28, 2013, which is hereby incorporated by reference in its entirety. For another non-limiting example of such a treatment, BAT can be activated using light. Exemplary embodiments of using light to activate BAT are described in more detail in U.S. Pat. Pub. No. 2014/0088487 entitled "Methods And Devices For Activating Brown Adipose Tissue Using Light" filed Jun. 28, 2013, which is hereby incorporated by reference in its entirety. For yet another non-limiting example of such a treatment, BAT can be chemically stimulated. Exemplary embodiments of using one or more chemicals to activate BAT are described in more detail in U.S. Pat. Pub. No. 2014/0018767 entitled "Methods And Devices For Activating Brown Adipose Tissue With Targeted Substance Delivery" filed Jun. 28, 2013, which is hereby incorporated by reference in its entirety. For another non-limiting example of such a treatment, brown adipocytes can be modified to increase activation of BAT, e.g., increasing a number of BAT adipocytes or increasing activation of BAT by modifying brown adipocytes to express a gene that activates brown adipocytes, such as UCP1. Exemplary embodiments of using modifying brown adipocytes to increase activation of BAT are described in more detail in U.S. Pat Pub. No. 2014/0199278 entitled "Brown Adipocyte Modification" filed Jun. 28, 2013, which is hereby incorporated by reference in its entirety. Other non-limiting examples of such a treatment include the patient being heated, a magnetic field being targeted to a region of a patient, the patient engaging in weight loss therapies, and/or a surgical procedure being performed on the patient, such as a procedure to induce weight loss and/or to improve metabolic function, e.g., glucose homeostatis, lipid metabolism, immune function, inflammation/anti-inflammatory balance, etc. Non-limiting examples of such weight loss therapies include a prescribed diet and prescribed exercise. Non-limiting examples of such a surgical procedure include gastric bypass, biliopancreatic diversion, a gastrectomy (e.g., vertical sleeve gastrectomy, etc.), adjustable gastric banding, vertical banded gastroplasty, intragastric balloon therapy, gastric plication, Magenstrasse and Mill, small bowel transposition, biliary diversion, vagal nerve stimulation, gastrointestinal barrier (e.g., duodenal endoluminal barrier, etc.), and procedures that allow for removal of food from the gastrointestinal tract.

Combining one or more treatments, particularly a weight loss therapy or a weight loss surgical procedure which does not activate BAT, e.g., a procedure other than RYGB, biliopancreatic diversion (BPD) with or without duodenal switch, or some duodenal or other intestinal barrier (e.g., a prescribed diet and/or exercise program, adjustable gastric banding, vertical banded gastroplasty, sleeve gastrectomy, gastric plication, Magenstrasse and Mill, intragastric balloon therapy, some duodenal or other intestinal barrier, and small bowel transposition, with a means for acute or chronic activation of BAT such as the nerve stimulation discussed herein, can result in desirable patient outcomes through a combined approach.

Because BAT activation may lead to an increase in body temperature locally, regionally, or systemically, transcutaneous and/or direct stimulation of nerves innervating BAT can be combined with one or more heat dissipation treatments, before and/or after transcutaneous and/or direct stimulation of BAT. Non-limiting examples of such a heat dissipation treatment include inducing cutaneous/peripheral vasodilation, e.g., local or systemic administration of Alpha antagonists or blockers, direct thermal cooling, etc.

Figure 4:
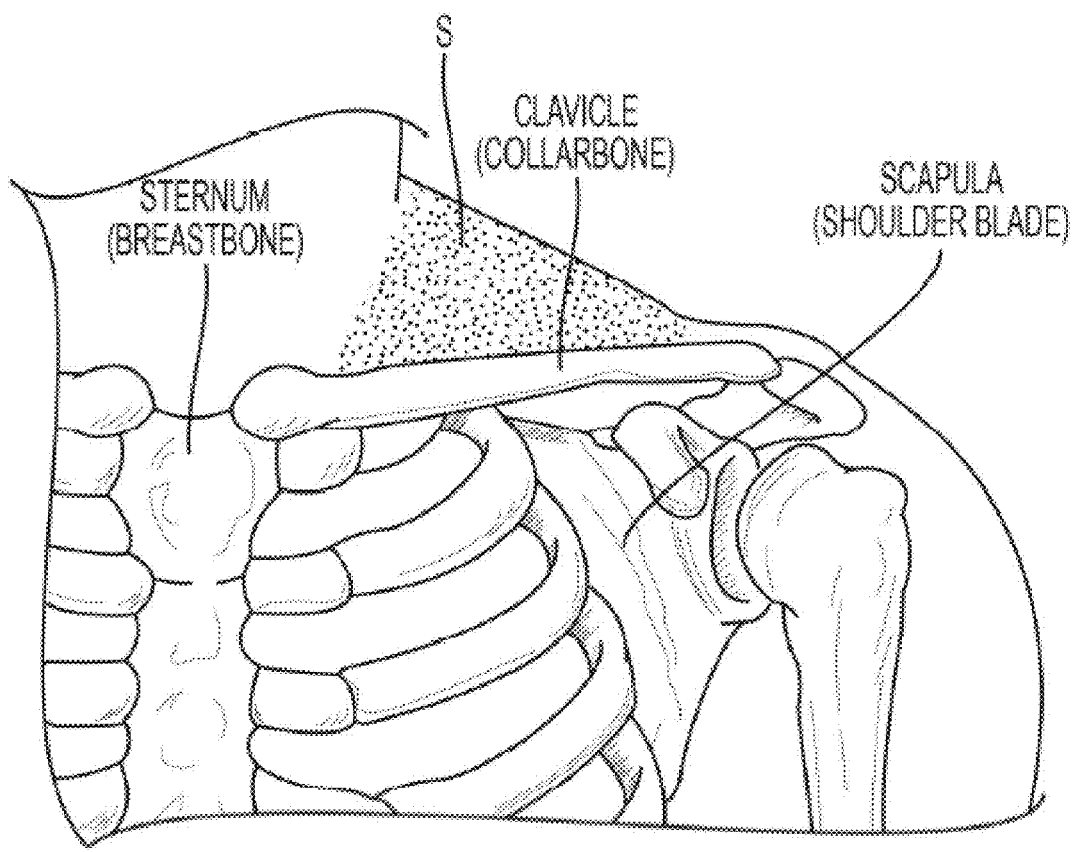
FIG. 4 is a transparent view of a portion of a human neck, chest, and shoulder area with a shaded supraclavicular region.

Whether BAT is activated directly and/or transcutaneously, target areas for BAT nerve stimulation and/or direct stimulation of brown adipocytes can include areas proximate to BAT depots, e.g., a supraclavicular region, the nape of the neck, over the scapula, alongside the spinal cord, near proximal branches of the sympathetic nervous system that terminate in BAT depots, and around at least one of the kidneys. Any BAT depot can be selected for activation. For non-limiting example, in one embodiment illustrated in FIG. 4, the device (not shown) can be positioned proximate to an area over a scapula in a supraclavicular region S. Identification of one or more BAT depots for activation can be determined on an individualized patient basis by locating BAT depots in a patient by imaging or scanning the patient using PET-CT imaging, tomography, thermography, MRI, or any other technique, as will be appreciated by a person skilled in the art. Non-radioactive based imaging techniques can be used to measure changes in blood flow associated with the activation of BAT within a depot. In one embodiment, a contrast media containing microbes can be used to locate BAT. The contrast media can be injected into a patient whose BAT has been activated. An energy sources such as low frequency ultrasound can be applied to the region of interest to cause destruction of bubbles from the contrast media. The rate of refill of this space can be quantified. Increased rates of refill can be associated with active BAT depots. In another embodiment, a contrast media containing a fluorescent media can be used to locate BAT. The contrast media can be injected into a patient whose BAT has been activated. A needle based probe can be placed in the region of interest that is capable of counting the amount of fluorescent contrast that passes the probe. Increased counts per unit time correspond to increased blood flow and can be associated with activated BAT depots. Because humans can have a relatively small amount of BAT and because it can be difficult to predict where BAT is most prevalent even near a typical BAT depot such as the nape of the neck, imaging a patient to more accurately pinpoint BAT depots can allow more nerves innervating BAT to be activated and with greater precision. Any number of BAT depots identified through patient imaging can be marked for future reference using a permanent or temporary marker. As will be appreciated by a person skilled in the art, any type of marker can be used to mark a BAT depot, e.g., ink applied on and/or below the epidermis, a dye injection, etc. The marker can be configured to only be visible under special lighting conditions such as an ultraviolet light, e.g., a black light.

Whether BAT is activated directly and/or transcutaneously, target cellular areas for BAT nerve activation and/or direct activation of brown adipocytes can include cell surface receptors (e.g., TGR5, $\beta_1 AR$, $\beta_2 AR$, $\beta_3 AR$, etc.), nuclear receptors (e.g., PPAR$\gamma$, FXR, RXR, etc.), transcription co-activators and co-repressors (e.g., PGC1$\alpha$, etc.), intracellular molecules (e.g., 2-deiodinase, MAP kinase, etc.), UCP1 activators, individual cells and related components (e.g., cell surface, mitochondria, and organelles), transport proteins, PKA activity, perilipin and HSL (phospho PKA substrate), CREBP (cAMP response element-binding protein), adenosine monophosphate-activated protein kinase (AMPK), bile acid receptors (e.g., TGR5, FGF15, FXR, RXR $\alpha$, etc.), muscarinic receptors, etc.

In the course of treating a patient, BAT nerves and/or brown adipocytes can be neuromodulated at any one or more BAT depots directly or indirectly and can be neuromodulated simultaneously, e.g., two or more BAT depots being concurrently activated, or activated sequentially, e.g., different BAT depots being activated at different times. Simultaneous neuromodulation of BAT can help encourage more and/or faster energy expenditure. Sequential neuromodulation of BAT can help prevent the "burning out" of target nerves and can help stimulate the creation of new BAT cells. Sequential nerve neuromodulation can include activating the same BAT depot more than once, with at least one other BAT depot being neuromodulation before activating a previously activated BAT depot. Simultaneous and/or sequential stimulation can help prevent tachypylaxis.

Figure 5:
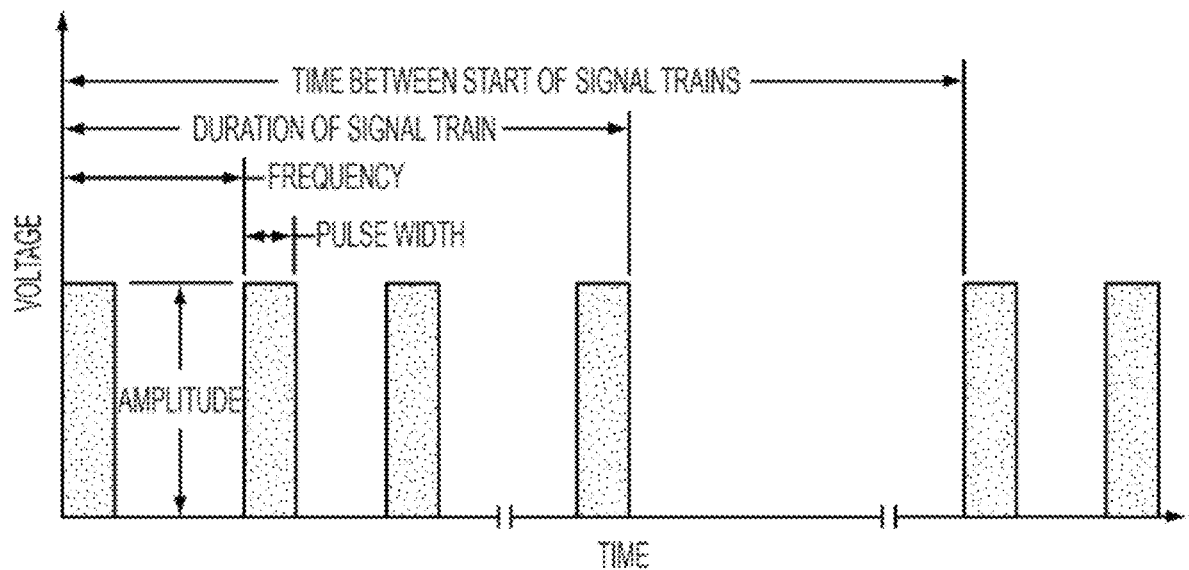
FIG. 5 is a graph showing voltage v. time for a generic electrical signal.

The electrical signal, whether transcutaneously or directly delivered, can be configured in a variety of ways. The stimulation "on" time amplitude can be higher for shorter periods and increased or decreased for longer periods of application. The electrical signal can have any "geometry" of the applied voltage, e.g., square waves, ramp waves, sine waves, triangular waves, and waveforms that contain multiple geometries. FIG. 5 illustrates amplitude, pulse width, activation signal pulse frequency, duration of signal train, and a time between start of signal trains for a generic (without any specified numerical parameters) electrical signal. For example, the electrical signal can have a current of at least about 50 mA, e.g., in a range of about 50 mA to 500 mA, in a range of about 50 mA to 100 mA, etc. For another example, the electrical signal can have a pulse width in a range of about 400 µs to 1000 µs. For yet another example, the electrical signal can have a frequency in a range of about 1 Hz to 50 Hz. For another example, the electrical signal can have a voltage having an amplitude in a range of about 1 to 20 V, e.g., about 10 V, e.g., about 4 V, about 7 V, etc.; a current having an amplitude in a range of about 2 to 6 mA, e.g., about 3 mA; a pulse width in a range about 10 µs to 40 ms, e.g., about 0.1 ms, about 2 ms, about 20 ms, etc.; an activation signal pulse frequency in a range of about 0.1 to 40 Hz, e.g., about 6 Hz or in a range of about 1 to 20 Hz; and a duration of signal train in a range of about 1 second to continuous, e.g., about 30 seconds, etc. Specific parameters for an electrical signal can be different based on where the electrical signal is delivered, e.g., based on whether an electrode delivering the electrical signal is transcutaneously placed or is implanted. In an exemplary embodiment of direct and/or subcutaneous stimulation of myelinated fibers, the electrical signal can have a current amplitude in a range of about 0.1 to 10 mA and a pulse width in a range of about 50 to 300 μsec. In general, a charge needed to stimulate myelinated fibers is less than a charge needed to stimulate unmyelinated fibers. In an exemplary embodiment of direct and/or subcutaneous stimulation of unmyelinated fibers, the electrical signal can have a current amplitude greater than and a pulse width at least as high as when applied to myelinated fibers, e.g., the first electrical signal having a current amplitude of greater than 10 mA and a pulse width of at least 300 μsec (e.g., a pulse width in a range of about 300 to 1000 μsec). In an exemplary embodiment of transcutaneous stimulation of myelinated fibers, the electrical signal can have a current amplitude of at least about 10 mA (e.g., in a range of about 10 to 100 mA) and a pulse width less than about 400 μsec. In general, current amplitudes above 100 mA can be uncomfortable for a patient. In an exemplary embodiment of transcutaneous stimulation of unmyelinated fibers, the electrical signal can have a current amplitude of at least about 50 mA (e.g., in a range of about 50 to 100 mA) and a pulse width in a range of about 400 to 1000 μsec. As will be appreciated by a person skilled in the art, the charge used to stimulate fibers can be adjusted by adjusting the current amplitude and the pulse width to achieve a desired charge. In general, in adjusting the charge, reducing the pulse width for the electrical signal can be beneficial over increasing the pulse width since very long pulse widths could cause damage and/or discomfort to the patient. A person skilled in the art will appreciate that a specific parameter may not have a precise numerical value but nevertheless be considered to be "about" that specific numerical value due to one or more factors, such as manufacturing tolerances of a device that generates a signal having the specific parameter.

A time between start of signal trains for a noncontinuous electrical signal delivered to BAT can be of any regular, predictable duration, e.g., hourly, daily, coordinated around circadian, ultradian, or other cycles of interest, etc., such as about ten minutes or about ninety minutes, or can be of any irregular, unpredictable duration, e.g., in response to one or more predetermined trigger events, as discussed further below. Embodiments of continuously delivering an electrical signal to BAT and embodiments of non-continuously delivering an electrical signal to BAT are further described in U.S. Pat. Pub. No. 2011/0270360 entitled "Methods And Devices For Activating Brown Adipose Tissue Using Electrical Energy" filed Dec. 29, 2010.

In one embodiment, the same electrical signal can be delivered to a particular BAT depot, either continuously or sequentially. In another embodiment, a first electrical signal can be transcutaneously or directly delivered to a particular BAT depot, and then subsequently, either immediately thereafter or after a passage of a period of time, a second, different electrical signal can be delivered to the same particular BAT depot. In this way, chances of a BAT depot adapting to a particular electrical signal can be reduced, thereby helping to prevent the BAT depot from becoming less receptive to electrical stimulation.

Whether a continuous electrical signal or an intermittent electrical signal is transcutaneously delivered, e.g., with a transdermal patch as discussed further below, or subcutaneously delivered via an at least partially implanted device, the electrical signal can include a low frequency modulating signal and a high frequency carrier signal. Generally, the high frequency carrier signal can be used to pass through high impedance tissue (subcutaneous or transcutaneous) while the modulating signal can be used to activate nervous tissue and/or electrically responsive brown adipocytes. The waveform can be generated by modulating a carrier waveform with a pulse envelope. Properties of the carrier waveform such as amplitude, frequency, and the like, can be chosen so as to overcome the tissue impedance and the stimulation threshold of the target nerve. The pulse envelope can be a waveform having a specific pulse width, amplitude and shape designed to selectively stimulate the target nerve. This waveform can be able to penetrate efficiently through tissue, such as skin, to reach the target nerve with minimal loss in the strength of the electrical signal, thereby saving battery power that would otherwise have been used in several attempts to stimulate the target nerve with low frequency signals. Moreover, only the target nerve is stimulated, and non-target nerves, e.g., nerves associated with pain, are not stimulated.

Exemplary embodiments of methods and devices for applying a signal including a high frequency carrier signal are described in more detail in U.S. Pat. Pub. No. 2011/0270360 entitled "Methods And Devices For Activating Brown Adipose Tissue Using Electrical Energy" filed Dec. 29, 2010, U.S. Pat. Pub. No. 2009/0093858 filed Oct. 3, 2007 and entitled "Implantable Pulse Generators And Methods For Selective Nerve Stimulation," U.S. Pat. Pub. No. 2005/0277998 filed Jun. 7, 2005 and entitled "System And Method For Nerve Stimulation," and U.S. Pat. Pub. No. 2006/0195153 filed Jan. 31, 2006 and entitled "System And Method For Selectively Stimulating Different Body Parts."

Figure 6:
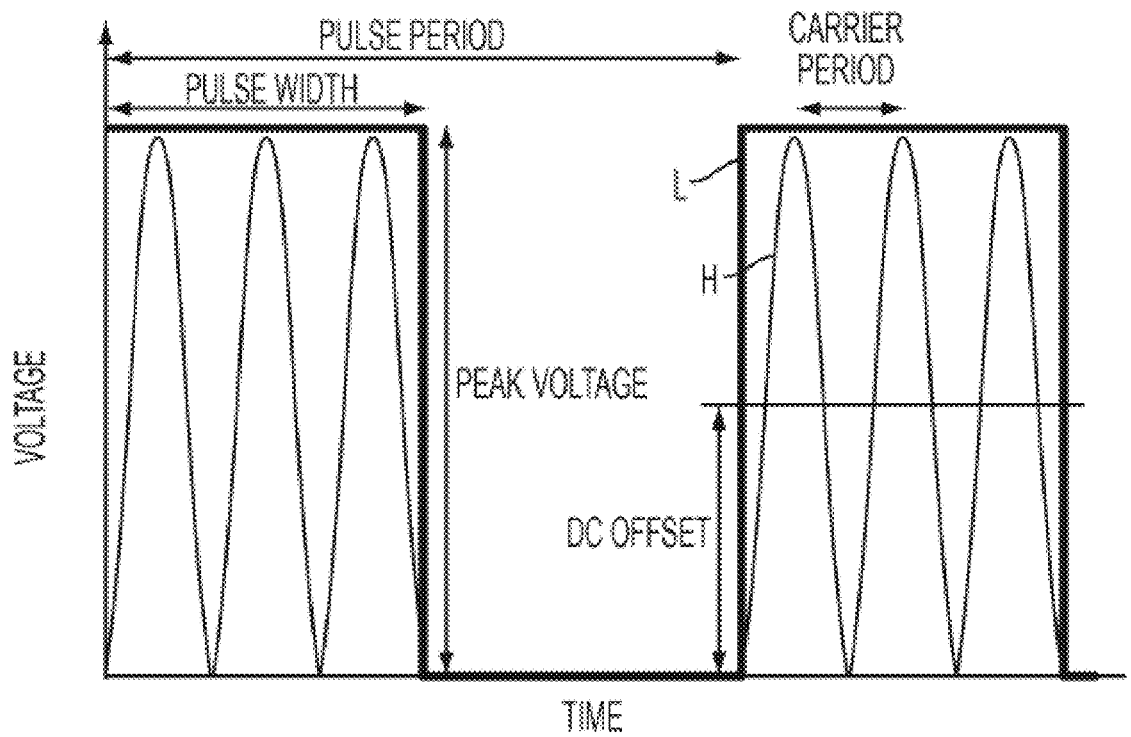
FIG. 6 is a graph showing voltage v. time for a generic electrical signal including a low frequency modulating signal and a high frequency carrier signal.

The low frequency modulating signal and a high frequency carrier signal can each have a variety of values and configurations. The low frequency modulating signal can be, e.g., a signal having an activation signal pulse frequency in a range of about 0.1 to 100 Hz, e.g., in a range of about 0.1 to 40 Hz, e.g., less than about 10 Hz. The high frequency carrier signal can be, e.g., in a range of about 10 to 400 kHz, e.g., in a range of about 200 to 250 kHz. Pulse widths can also vary, e.g., be in a range of about 10 μs to 10 ms, e.g., less than about 2 ms. In one exemplary embodiment, the electrical signal can have a modulating signal in a range of about 2 to 15 Hz, e.g., about 6 Hz, a carrier frequency of about 210 kHz, and a pulse width in a range of about 0.1 to 2 ms. FIG. 6 illustrates a generic (without any specified numerical parameters) electrical signal including a low frequency modulating signal L and a high frequency carrier signal H.

Generally, low frequency signals can cause activation of Types A and B fibers, e.g., myelinated neurons, and Type C fibers, e.g., unmyelinated neurons. The signal to activate Type C fibers can be greater than, e.g., a longer pulse width and a higher current amplitude, than a signal to activate Type A and B fibers. Postganglionic fibers innervating BAT depots likely include Type C fibers, thereby allowing a BAT depot to be activated by a low frequency signal, e.g., a signal less than about 10 Hz and having a pulse width greater than about 300 μs. Preganglionic nerves such as small diameter, unmyelinated Type C fibers and small diameter, myelinated Type B fibers may also innervate BAT, thereby also allowing a BAT depot to be activated by a low frequency signal, e.g., a signal in a range of about 10 to 40 Hz and having a pulse width less than about 200 μs.

An electrical signal delivered to a BAT depot can be applied continuously, in predetermined intervals, in sporadic or random intervals, in response to one or more predetermined trigger events, or in any combination thereof. If the signal is continuously delivered to the patient, particular care should be taken to ensure that the signal delivered to the patient will not damage the target nerves or tissues. For one non-limiting example, nerve or tissue damage can be reduced, if not entirely prevented, by continuously delivering an electrical signal via en electrode having a relatively large surface area to help distribute an electrical signal's energy between multiple nerves. For electrical signals delivered intermittently, nerve damage can be reduced, if not entirely prevented, by selecting an on/off ratio in which the signal is "off" for more time than it is "on." For non-limiting example, delivering an electrical signal to BAT intermittently with an on/off ratio of about 1:19, e.g., electrical signals delivered for 30 seconds every ten minutes (30 seconds on/9.5 minutes off), can help reduce or entirely prevent nerve damage.

The device delivering the electrical signal can be configured to respond to one or more predetermined trigger events, e.g., events that are sensed by or otherwise signaled to the device. Non-limiting examples of trigger events include the patient eating, the patient resting (e.g., sleeping), a threshold temperature of the patient (e.g., a temperature in the stimulated BAT depot or a core temperature), a directional orientation of the patient (e.g., recumbent as common when sleeping), a change in the patient's weight, a change in the patient's tissue impedance, manual activation by the patient or other human (e.g., via an onboard controller, via a wired or wirelessly connected controller, or upon skin contact), a blood chemistry change in the patient (e.g., a hormonal change), low energy expenditure, menstrual cycles in women, medication intake (e.g., an appetite suppressant such as topiramate, fenfluramine, etc.), an ultradian or other circadian rhythm of the patient, and a manually-generated or automatically-generated signal from a controller in electronic communication, wired and/or wireless, with the device. In one embodiment, the patient eating can be determined through a detection of heart rate variability, as discussed in more detail in U.S. Pat. No. 8,696,616 filed on Dec. 29, 2010 entitled "Obesity Therapy And Heart Rate Variability" and U.S. Pat. Pub. No. 2012/0172783 filed on Dec. 29, 2010 and entitled "Obesity Therapy And Heart Rate Variability," which are hereby incorporated by reference in their entireties. The controller can be internal to the device, be located external from but locally to device, or be located external and remotely from device. As will be appreciated by a person skilled in the art, the controller can be coupled to the device in any way, e.g., hard-wired thereto, in wireless electronic communication therewith, etc. In some embodiments, multiple devices can be applied a patient, and at least two of those devices can be configured to deliver an electrical signal based on different individual trigger events or combinations of trigger events.

Figure 7:
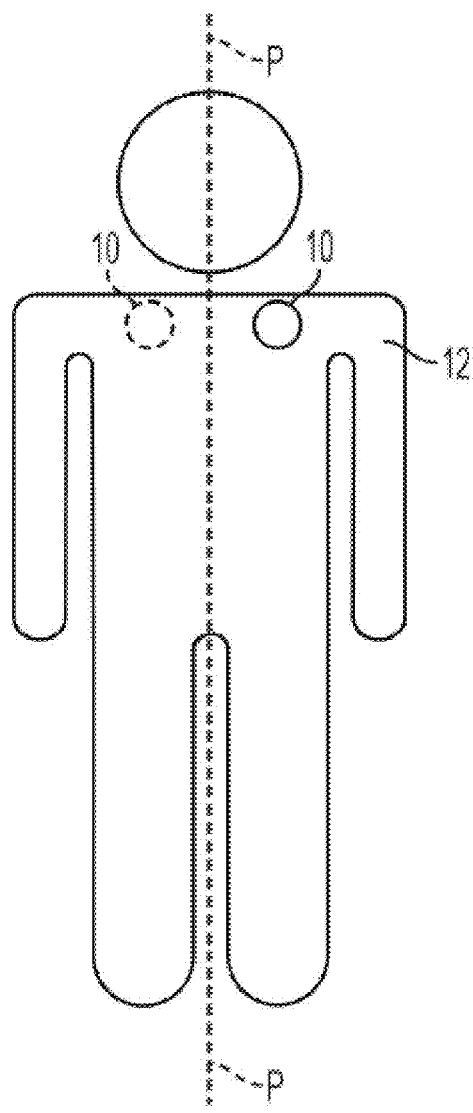
FIG. 7 is a front view of a body showing one embodiment of an electrical stimulation device positioned on opposite sides of the body's sagittal plane.

Generally, transcutaneous stimulation of BAT can include applying a device to an exterior skin surface of a patient proximate to a BAT depot and activating the device to deliver an electrical signal to the BAT depot. In this way, the electrical signal can activate the BAT proximate to the device by stimulating the nerves innervating the BAT and/or by stimulating brown adipocytes directly. As mentioned above, two or more transcutaneous devices, same or different from one another, can be simultaneously applied to a patient, proximate to the same BAT depot or to different BAT depots. Although a patient can have two or more transcutaneously applied devices and although the devices can be configured to simultaneously deliver electrical signals to BAT, the devices can be configured such that only one delivers an electrical signal at a time. As also mentioned above, a transcutaneous device can be rotated to different BAT depots of a patient and deliver an electrical signal to each of the BAT depots. Rotating a device between two or more different locations on a patient's body and/or removing a device from a patient when not in use can help prevent nerve or tissue desensitization and/or dysfunction, can help reduce any adverse effects of a device's attachment to the body, e.g., irritation from an adhesive applying a device to skin, and/or can help stimulate creation or replication of new BAT in multiple locations on a patient's body. For non-limiting example, the device can be placed in varying positions on the body to modulate the activity of different regions of BAT. In one embodiment, the device can be worn on one side of the neck, e.g., the left side, for a period of time and then on an opposite side of the neck, e.g., the right side, for the next time period, etc. In another embodiment, the device can be worn on an anterior side of a BAT depot, e.g., front of a left shoulder on one side of the patient's coronal plane, for a period of time and then on an opposite, posterior side of the BAT depot, e.g., back of the left shoulder on the opposite side of the patient's coronal plane, for the next period of time. In yet another embodiment, illustrated in FIG. 7, a device 10 can be worn proximate a BAT depot on one of a left and right side of a sagittal plane P in a supraclavicular region of a body 12 for a period of time and then the device 10 can be worn on the other of the left and right sides of the sagittal plane P in the supraclavicular region proximate to another BAT depot for the next period of time. Although the same device 10 is shown in FIG. 7 as being sequentially relocated to different tissue surface or skin positions on the body 12, as discussed herein, one or both of the devices can be implanted and/or two separate devices can be used with a patient such that a first device is positioned at one location and a second device is positioned at a second, different location.

In one embodiment, a transcutaneous device can be positioned in a first location on a patient, e.g., a left supraclavicular region, for a first predetermined period of time, e.g., one week, and then relocated to a second location on the patient, e.g., a right supraclavicular region, for a second predetermined period of time, e.g., one week. The first and second predetermined periods of time can be the same as or different from one another. The first and second locations can mirror each other, e.g., on left and rights of a sagittal plane of the patient, or they can non-mirror images of one another. During the first predetermined period of time, the device can be configured to cycle in a diurnal pattern during waking hours between being "on" to electrically stimulate the patient, e.g., a 30 minute dose of electrical stimulation having any of the parameters discussed herein, and being "off" without delivering electrical stimulation to the patient, e.g., a one hour period of no stimulation. The electrical signal, e.g., an electrical signal including modulating and carrier signals, delivered when the device is "on" can be continuous, can ramp up at a start of the "on" time to a predetermined maximum level, such as a level set by a physician during an initial patient visit, can ramp down at an end of the "on" time, and can be substantially constant between the ramp up and ramp down times. The signal can ramp up and down in any amount of time, e.g., in less than about five minutes. Such a cycle can be repeated about twelve time per day during each of the first and second predetermined periods of time, and during any subsequent periods of time, e.g., repeatedly switching the device every other week between the first and second locations.

In another embodiment, a transcutaneous device can be positioned on an exterior skin surface of a patient and be configured to electrically stimulate the patient in a natural mimicking pattern for a time period of at least one week. The device can be relocated to a different location on the patient's skin and stimulate the patient at the different location in the natural mimicking pattern for another time period of at least one week. The device can continue being located and relocated for any number of weeks. The electrical stimulation can include a fixed carrier frequency and a variable modulating frequency configured to vary based on nutrient and mechanoreceptors that indicate the patient eating. In other words, the modulating frequency can mimic stomach distension of the patient.

In still another embodiment, a transcutaneous device can be positioned on an exterior skin surface of a patient and be configured to intermittently electrically stimulate the patient at a constant intensity, e.g., cycle between an "on" configuration delivering an electrical signal at the constant intensity to the patient and an "off" configuration without delivering any electrical signal to the patient. The delivered electrical signal can ramp up at a start of an "on" time period to the constant intensity, and can ramp down at an end of the "on" time period from the constant intensity. The signal can ramp up and down in any amount of time, such as ramp up for about ¼ of a total "on" time, deliver the signal at the constant intensity for about ½ of the total "on" time, and ramp down for about ¼ of the total "on" time. In one embodiment, the device can ramp up from about 0 Hz to about 20 Hz in about 15 minutes, stimulate at about 20 Hz for about 35 minutes, and ramp down from about 20 Hz to about 0 Hz in about 10 minutes for a total "on" time of about 50 minutes.

The transcutaneous device used to transcutaneously activate BAT can have a variety of sizes, shapes, and configurations. Generally, the device can be configured to generate and/or deliver an electrical signal to tissue at predetermined intervals, in response to a manual trigger by the patient or other human, in response to a predetermined trigger event, or any combination thereof. As will be appreciated by a person skilled in the art, and as discussed in more detail above and in U.S. Pat. Pub. No. 2009/0093858 filed Oct. 3, 2007 and entitled "Implantable Pulse Generators And Methods For Selective Nerve Stimulation," the body attenuates low frequency signals requiring a high frequency signal for transdermal passage. This high-frequency or carrier signal, in conjunction with a modulating low frequency wave can be applied by the transcutaneous device to stimulate the nerves innervating BAT for FFA or other lipid consumption leading to loss of body fat and body weight, increased metabolic rate, and/or comorbidity improvement.

Figure 8:
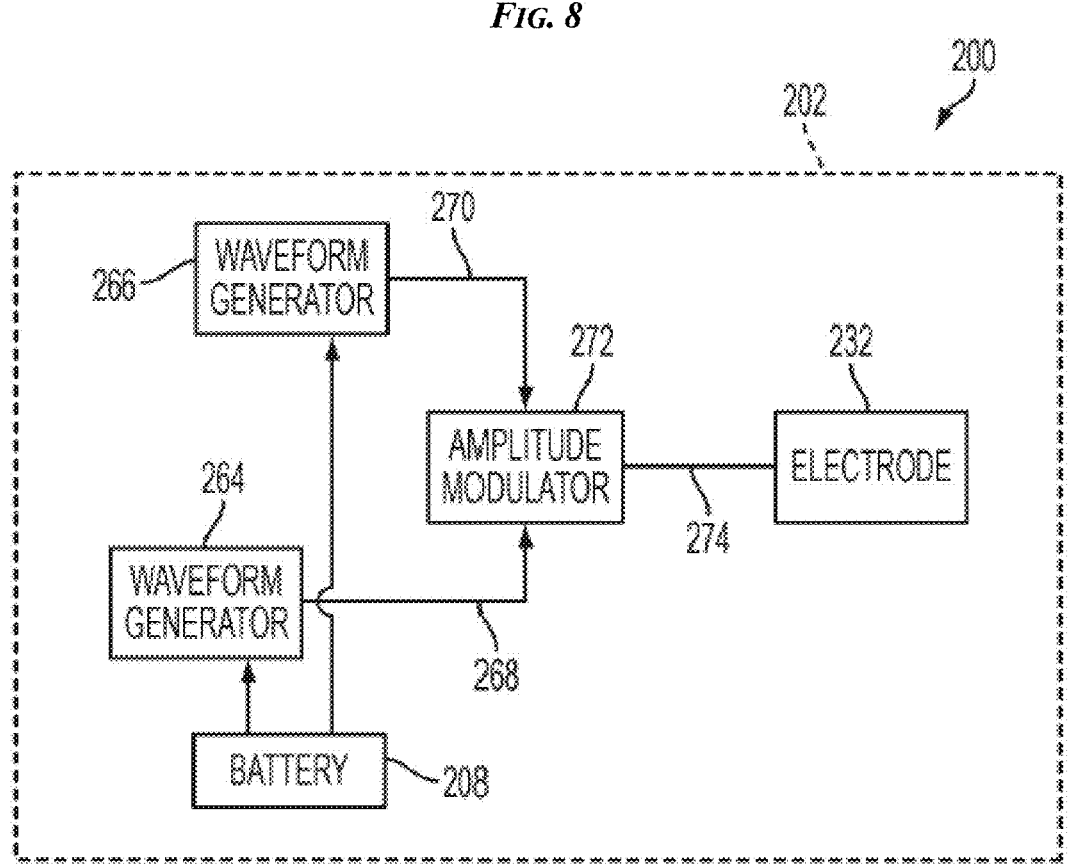
FIG. 8 is a schematic view of one embodiment of a transcutaneous device for neuromodulating BAT.

FIG. 8 illustrates one exemplary embodiment of a transcutaneous device 200 in the form of a selective nerve stimulation patch housing configured to generate and deliver an electrical signal to tissue such as BAT. The device 200 includes a circuitized substrate 202 configured to generate electrical signals for stimulating tissue such as BAT. The device 200 can include a suitable power source or battery 208, e.g., a lithium battery, a first waveform generator 264, and a second waveform generator 266. The first and second waveform generators 264, 266 can be electrically coupled to and powered by the battery 208. The waveform generators 264, 266 can be of any suitable type, such as those sold by Texas Instruments of Dallas, Tex. under model number NE555. The first waveform generator 264 can be configured to generate a first waveform or low frequency modulating signal 268, and the second waveform generator 266 can be configured to generate a second waveform or carrier signal 270 having a higher frequency than the first waveform 268. As discussed herein, such low frequency modulating signals cannot, in and of themselves, pass through body tissue to effectively stimulate target nerves. The second waveform 270 can, however, to overcome this problem and penetrate through body tissue. The second waveform 270 can be applied along with the first waveform 268 to an amplitude modulator 272, such as the modulator having the designation On-Semi MC1496, which is sold by Texas Instruments.

Figure 9:
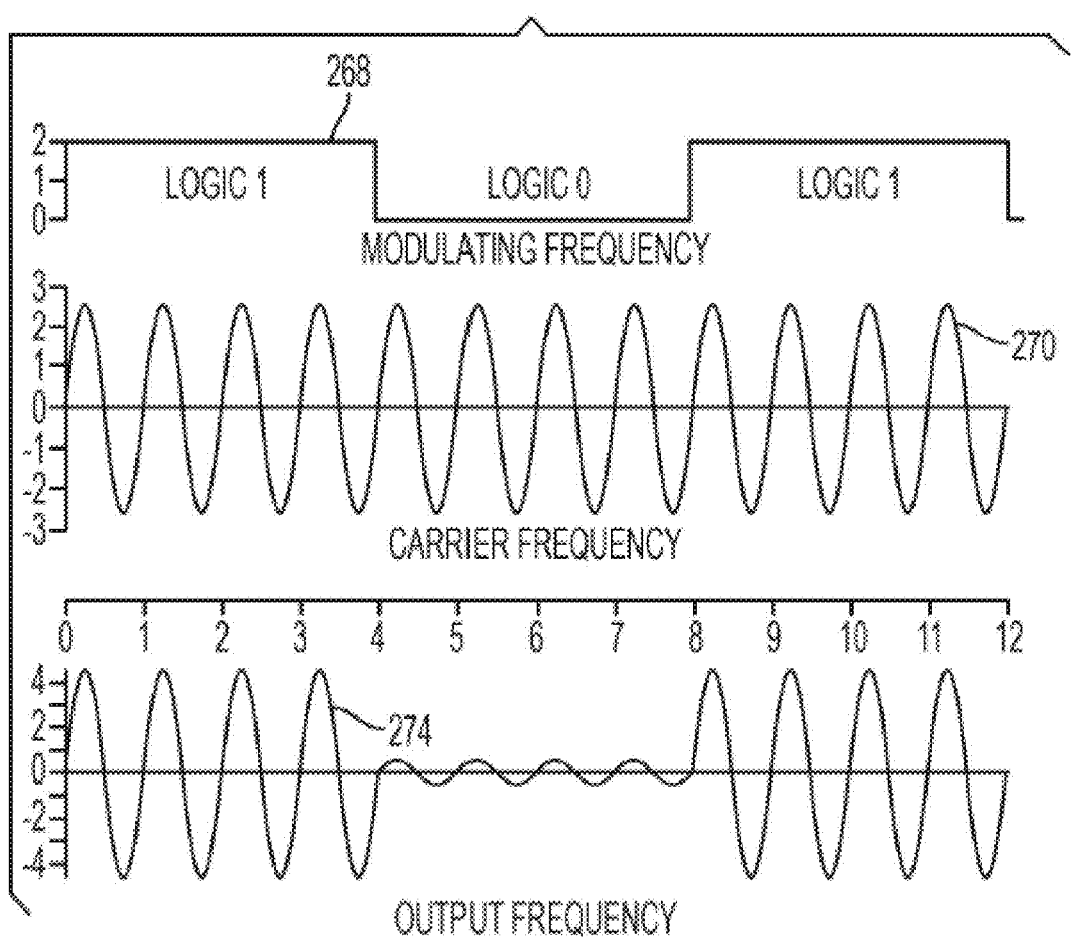
FIG. 9 is a plurality of graphs showing exemplary waveforms generated by the transcutaneous device of FIG. 8.

The modulator 272 can be configured to generate a modulated waveform 274 that is transmitted to one or more electrodes 232 accessible at a bottom surface of the circuitized substrate 202. Although FIG. 8 shows only one electrode 232, the device 200 can include two or more electrodes. The electrodes 232 can be configured to, in turn, apply the modulated waveform 274 to a target nerve to stimulate the target nerve. As illustrated in FIGS. 8 and 9, the first waveform 268 can be a square wave, and the second waveform 270 can be a sinusoidal signal. As will be appreciated by a person skilled in the art, modulation of the first waveform 268 with the second waveform 270 can results in a modulated waveform or signal 274 having the configuration shown in FIG. 9. Although the signals in FIG. 9 are illustrated as being biphasic, the signals can be monophasic.

Various exemplary embodiments of transcutaneous devices configured to apply an electrical signal or other stimulation means to stimulate nerves are described in more detail in U.S. Pat. Pub. No. 2011/0270360 entitled "Methods And Devices For Activating Brown Adipose Tissue Using Electrical Energy" filed Dec. 29, 2010, U.S. Pat. Pub. No. 2009/0132018 filed Nov. 16, 2007 and entitled "Nerve Stimulation Patches And Methods For Stimulating Selected Nerves," U.S. Pat. Pub. No. 2008/0147146 filed Dec. 19, 2006 and entitled "Electrode Patch And Method For Neurostimulation," U.S. Pat. Pub. No. 2005/0277998 filed Jun. 7, 2005 and entitled "System And Method For Nerve Stimulation," U.S. Pat. Pub. No. 2006/0195153 filed Jan. 31, 2006 and entitled "System And Method For Selectively Stimulating Different Body Parts," U.S. Pat. Pub. No. 2007/0185541 filed Aug. 2, 2006 and entitled "Conductive Mesh For Neurostimulation," U.S. Pat. Pub. No. 2006/0195146 filed Jan. 31, 2006 and entitled "System And Method For Selectively Stimulating Different Body Parts," U.S. Pat. Pub. No. 2008/0132962 filed Dec. 1, 2006 and entitled "System And Method For Affecting Gastric Functions," U.S. Pat. Pub. No. 2008/0147146 filed Dec. 19, 2006 and entitled "Electrode Patch And Method For Neurostimulation," U.S. Pat. Pub. No. 2009/0157149 filed Dec. 14, 2007 and entitled "Dermatome Stimulation Devices And Methods," U.S. Pat. Pub. No. 2009/0149918 filed Dec. 6, 2007 and entitled "Implantable Antenna," U.S. Pat. Pub. No. 2009/0132018 filed Nov. 16, 2007 and entitled "Nerve Stimulation Patches And Methods For Stimulating Selected Nerves," U.S. patent application Ser. No. 12/317,193 filed Dec. 19, 2008 and entitled "Optimizing The Stimulus Current In A Surface Based Stimulation Device," U.S. patent application Ser. No. 12/317,194 filed Dec. 19, 2008 and entitled "Optimizing Stimulation Therapy Of An External Stimulating Device Based On Firing Of Action Potential In Target Nerve," U.S. patent application Ser. No. 12/407,840 filed Mar. 20, 2009 and entitled "Self-Locating, Multiple Application, And Multiple Location Medical Patch Systems And Methods Therefor," U.S. Pat. Pub. No. 2011/0094773 filed Oct. 26, 2009 and entitled "Offset Electrode," and U.S. Pat. No. 8,812,100 filed May 10, 2012 and entitled "A Device And Method For Self-Positioning Of A Stimulation Device To Activate Brown Adipose Tissue Depot In Supraclavicular Fossa Region."

In an exemplary embodiment, the transcutaneous device can include an electrical stimulation patch configured to be applied to an external skin surface and to deliver an electrical signal to tissue below the skin surface, e.g., to underlying BAT. The patch can be configured to generate its own electrical signal with a signal generator and/or to deliver an electrical signal received by the patch from a source in electronic communication with the patch. The device can be wireless and be powered by an on-board and/or external source, e.g., inductive power transmission. The patch can be attached to the skin in any way, as will be appreciated by a person skilled in the art. Non-limiting examples of patch application include using a skin adhesive locally (e.g., on patch rim), using a skin adhesive globally (e.g., on skin-contacting surfaces of the patch), using an overlying support (e.g., gauze with taped edges), using an adherent frame allowing interchangeability (e.g., a brace or an article of clothing), being subdermally placed with wireless connectivity (e.g., Bluetooth) or transdermal electrodes, and using any combination thereof. Electrodes can include receiver circuitry configured to interact with a controller in electronic communication with the electrodes such that the controller can control at least some functions of the electrodes, e.g., on/off status of the electrodes and adjustment of parameters such as amplitude, frequency, length of train, etc.

In use, and as mentioned above, an electrical stimulation patch can be worn continuously or intermittently as needed. In a transcutaneous application, a patch such as one described in previously mentioned U.S. Pat. Pub. No. 2009/0132018, can be designed to transmit through the skin using a dual waveform approach employing a first waveform designed to stimulated a nerve coupled with a high frequency carrier waveform. The patch can be placed proximate to a BAT depot, such as over the left supraclavicular region of the patient's back, for a predetermined amount of time, e.g., twelve hours, one day, less than one week, seven days (one week), one month (four weeks), etc., and can continuously deliver an electrical signal to the BAT. As mentioned above, the BAT depot can be identified by imaging the patient prior to application of the patch proximate to the BAT depot. Seven days is likely the longest period an adhesive can be made to stick to the skin of a patient without modification and can thus be a preferable predetermined amount of time for patches applied to skin with an adhesive. After the predetermined amount of time, the patch can be removed by a medical professional or the patient, and the same patch, or more preferably a new patch, can be placed, e.g., on the right supraclavicular region of the patient's back for another predetermined amount of time, which can be the same as or different from the predetermined amount of time as the first patch applied to the patient. This process can be repeated for the duration of the treatment, which can be days, weeks, months, or years. In some embodiments, the process can be repeated until occurrence of at least one threshold event, e.g., a predetermined amount of time, a predetermined physiological effect such as a predetermined amount of weight lost by the patient, etc. If the same patch is relocated from a first region, e.g., the left supraclavicular region, to a second region, right supraclavicular region, the patch can be reconditioned after removal from the first region and prior to placement at the second region. Reconditioning can include any one or more actions, as will be appreciated by a person skilled in the art, such as replacing one or more patch components, e.g., a battery, an adhesive, etc.; cleaning the patch; etc.

To more accurately simulate a weight loss surgery that has a continuous or chronic effect on a patient for an extended period of time, the patch can be placed on a patient and continuously or chronically deliver an electrical signal thereto for an extended, and preferably predetermined, amount of time. In an exemplary embodiment, the predetermined amount of time can be at least four weeks. The electrical signal can be delivered to same BAT depot for the predetermined amount of time, or two or more different BAT depots can be stimulated throughout the predetermined amount of time, e.g., left and right supraclavicular regions being stimulated for alternate periods of seven days to total one month of predetermined time. Continued or chronic nerve stimulation to activate BAT can increase BAT energy expenditure over time and potentially induce more or faster weight loss, a faster metabolic rate, and/or better comorbidity improvement than periodic or intermittent nerve stimulation. The electrical signal can be the same or can vary during the amount of time such that the electrical signal is continuously and chronically applied to the patient to provide 24/7 treatment mimicking the 24/7 consequences of surgery. The continuous amount of time the patient is electrically stimulated can be a total amount of continuous activation of any one BAT depot (e.g., activation of a single BAT depot), sequential activation of two or more BAT depots, simultaneous activation of two or more BAT depots, or any combination thereof. A total amount of time of sequential activation of different BAT depots can be considered as one extended amount of time despite different areas of BAT activation because activation of one BAT depot may cause the brain to signal for BAT activation in other BAT depots.

Generally, direct activation of BAT can include implanting a device below the skin surface proximate to a BAT depot, e.g., within a BAT depot, and activating the device to deliver an electrical signal to the nerves innervating the BAT depot and/or to brown adipocytes directly. BAT itself is densely innervated, with each brown adipocyte being associated with its own nerve ending, which suggests that stimulating the BAT directly can target many if not all brown adipocytes and depolarize the nerves, leading to activation of BAT. The sympathetic nerves that innervate BAT can be accessed directly through standard surgical techniques, as will be appreciated by a person skilled in the art. The device can be implanted on a nerve or placed at or near a nerve cell's body or perikaryon, dendrites, telodendria, synapse, on myelin shelth, node of Ranvier, nucleus of Schwann, or other glial cell to stimulate the nerve. While implanting such a device can require a surgical procedure, such implantation is typically relatively short, outpatient, and with greatly reduced risks from longer and more complicated surgical procedures such as gastric bypass. In an exemplary embodiment, a stimulation device with at least two electrodes can be at least partially implanted in the patient (e.g., an implanted electrode array in communication with an external stimulator attached to a patient's skin; a percutaneous system such as a patch including a stimulator and being in communication with percutaneous electrodes coupled to a conductor (e.g., a needle, a conductive gel, etc.); etc.), and more preferably entirely within the patient (e.g., an implanted microstimulator including an electrode array, an implantable pulse generator (IPG), and a lead connecting the electrode array and the IPG; an implanted microstimulator including an integrated electrode array and IPG; etc.). One example of the patch includes the Smartpatch (SPR Therapeutics, Cleveland, Ohio). One example of the electrode array includes a flexible and flat array. A person skilled in the art will appreciate that any number of electrodes, e.g., one or more, can be at least partially implanted in the patient. The leads of the at least one electrode can be implanted in a location sufficiently close to the nerves innervating the BAT so that when activated, the signal sent through the at least one electrode is sufficiently transferred to adjacent nerves, causing these nerves to depolarize. As mentioned above, electrodes can include receiver circuitry configured to interact with a controller in electronic communication with the electrodes such that the controller can control at least some functions of the electrodes, e.g., on/off status of the electrodes and adjustment of parameters such as amplitude, frequency, length of train, etc.

Figure 10:
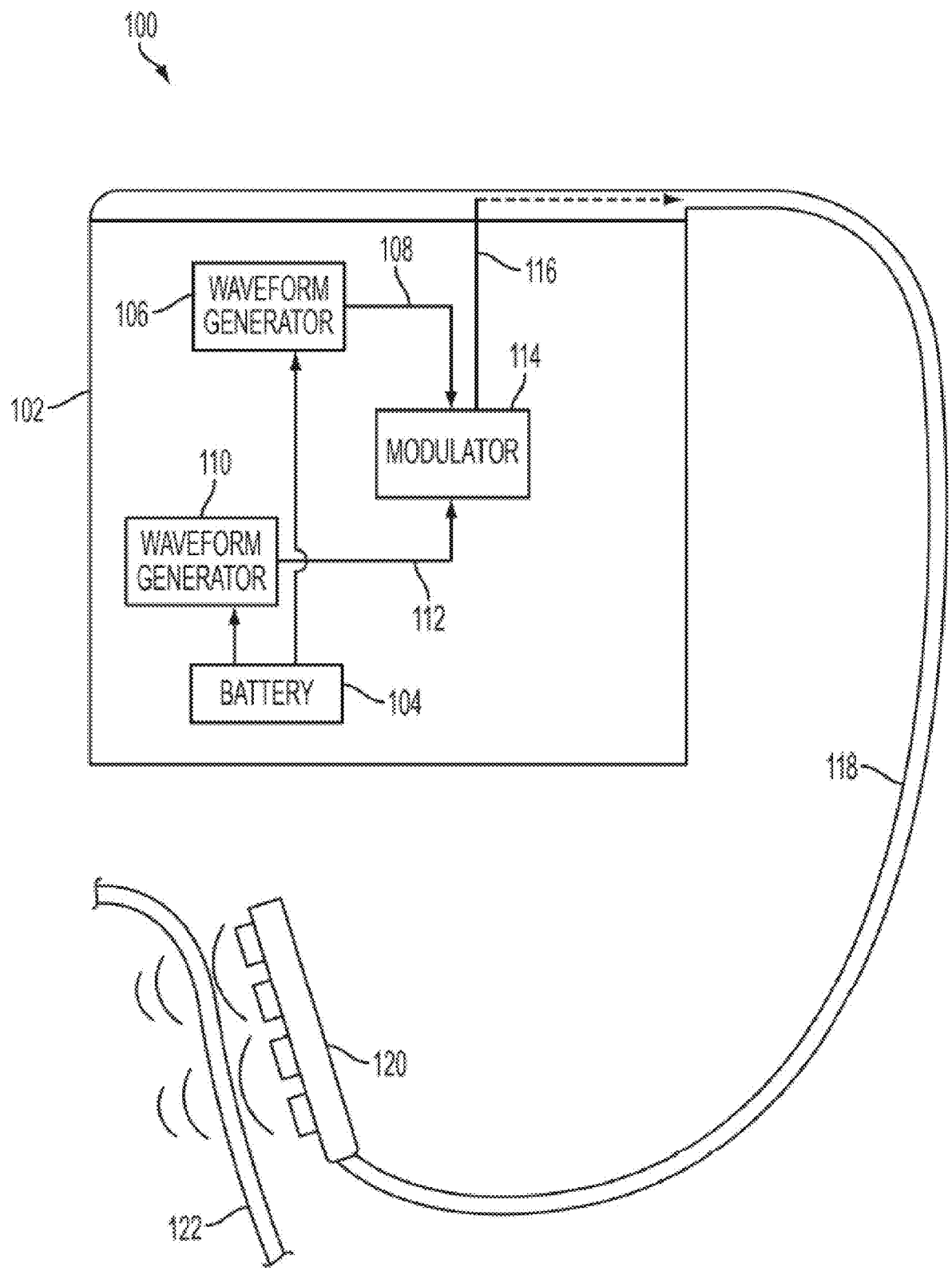
FIG. 10 is a schematic view of one embodiment of an implantable device for neuromodulating BAT.

FIG. 10 illustrates one exemplary embodiment of an implantable device 100 configured to generate and deliver an electrical signal to tissue such as BAT. The implantable device 100 can include a housing 102 coupled to a suitable power source or battery 104, such as a lithium battery, a first waveform generator 106, and a second waveform generator 110. As in the illustrated embodiment, the battery 104 and first and second waveform generators can be located within the housing 102. In another embodiment, a battery can be external to a housing and be wired or wirelessly coupled thereto. The housing 102 is preferably made of a biocompatible material. The first and second waveform generators 106, 110 can be electrically coupled to and powered by the battery 104. The waveform generators 106, 110 can be of any suitable type, such as those sold by Texas Instruments of Dallas, Tex. under model number NE555. The first waveform generator 106 can be configured to generate a first waveform or low frequency modulating signal 108, and the second waveform generator 110 can be configured to generate a second waveform or carrier signal 112 having a higher frequency than the first waveform 108. The carrier signal 112 can make it easier to stimulate BAT and/or nerves innervating BAT by using less energy, and/or can make the electrical signal more comfortable for the patient. As discussed herein, the first waveform 108 cannot easily, in and of themselves, pass through body tissue to effectively stimulate target nerves. The second waveform 112 can, however, help the electrical signal penetrate through body tissue. The second waveform 112 can be applied along with the first waveform 108 to an amplitude modulator 114, such as the modulator having the designation On-Semi MC1496, which is sold by Texas Instruments.

Figure 11:
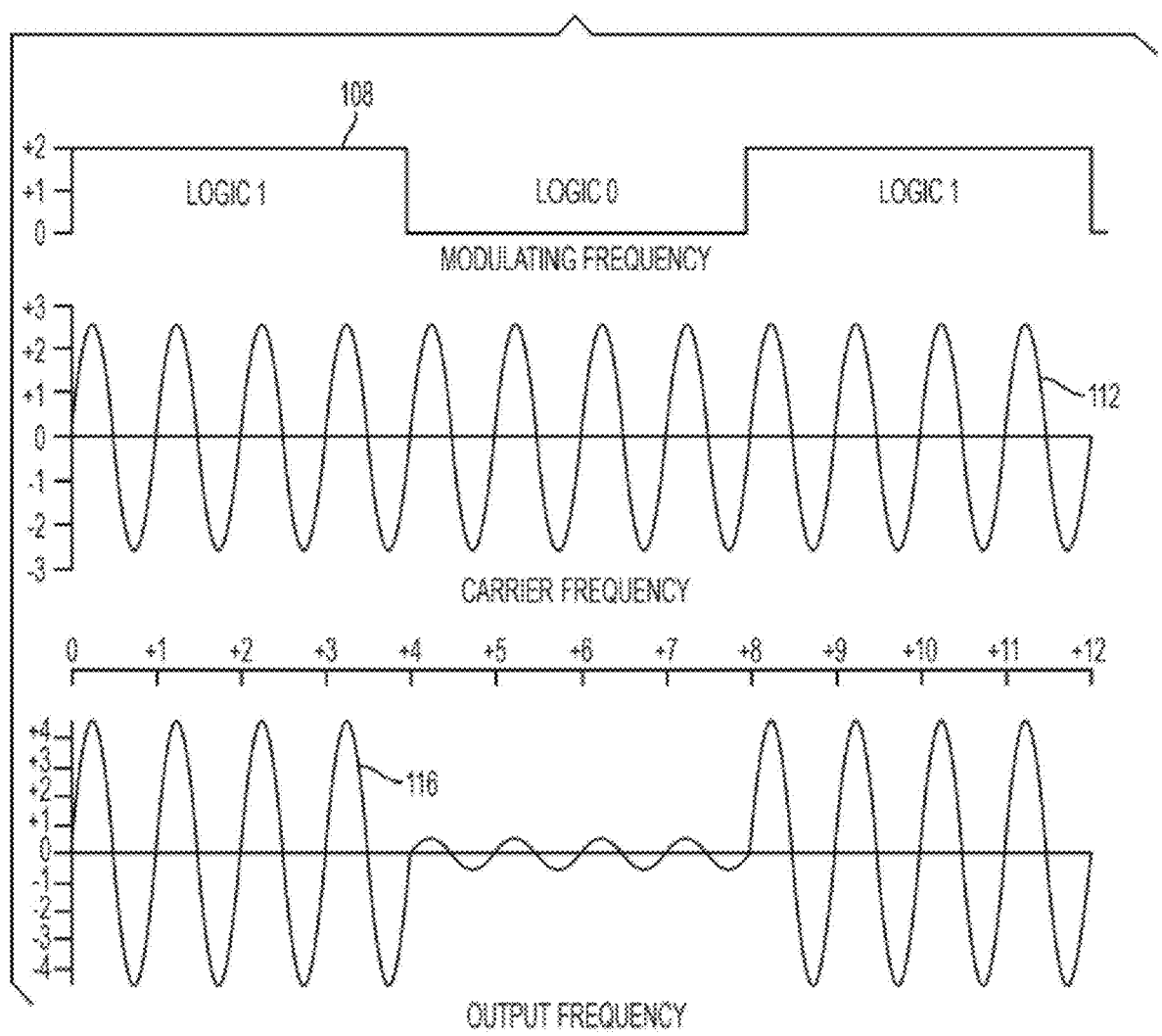
FIG. 11 is a plurality of graphs showing exemplary waveforms generated by the implantable device of FIG. 10.

The modulator 114 can be configured to generate a modulated waveform 116 that is transmitted through a lead 118 to one or more electrodes 120. Four electrodes are illustrated, but the device 100 can include any number of electrodes having any size and shape. The lead 118 can be flexible, as in the illustrated embodiment. The electrodes 120 can be configured to, in turn, apply the modulated waveform 116 to a target nerve 122 to stimulate the target nerve 122. As illustrated in FIGS. 6 and 11, the first waveform 108 can be a square wave, and the second waveform 112 can be a sinusoidal signal. As will be appreciated by a person skilled in the art, modulation of the first waveform 108 with the second waveform 112 can result in a modulated waveform or signal 116 having the configuration shown in FIG. 6.

If an electrode is implanted under a patient's skin, a waveform transmitted to the implanted electrode can include a modulating signal but not include a carrier signal because, if the implanted electrode is sufficiently near a BAT depot, the modulating signal alone can be sufficient to stimulate the target. The waveform transmitted to an implanted electrode can, however, include both a modulating signal and a carrier signal.

Various exemplary embodiments of devices configured to directly apply an electrical signal to stimulate nerves are described in more detail in U.S. Pat. Pub. No. 2011/0270360 entitled "Methods And Devices For Activating Brown Adipose Tissue Using Electrical Energy" filed Dec. 29, 2010, U.S. Pat. Pub. No. 2005/0177067 filed Jan. 26, 2005 and entitled "System And Method For Urodynamic Evaluation Utilizing Micro-Electronic Mechanical System," U.S. Pat. Pub. No. 2008/0139875 filed Dec. 7, 2006 and entitled "System And Method For Urodynamic Evaluation Utilizing Micro Electro-Mechanical System Technology," U.S. Pat. Pub. No. 2009/0093858 filed Oct. 3, 2007 and entitled "Implantable Pulse Generators And Methods For Selective Nerve Stimulation," U.S. Pat. Pub. No. 2010/0249677 filed Mar. 26, 2010 and entitled "Piezoelectric Stimulation Device," U.S. Pat. Pub. No. 2005/0288740 filed Jun. 24, 2004 and entitled, "Low Frequency Transcutaneous Telemetry To Implanted Medical Device," U.S. Pat. No. 7,599,743 filed Jun. 24, 2004 and entitled "Low Frequency Transcutaneous Energy Transfer To Implanted Medical Device," U.S. Pat. No. 7,599,744 filed Jun. 24, 2004 and entitled "Transcutaneous Energy Transfer Primary Coil With A High Aspect Ferrite Core," U.S. Pat. No. 7,191,007 filed Jun. 24, 2004 and entitled "Spatially Decoupled Twin Secondary Coils For Optimizing Transcutaneous Energy Transfer (TET) Power Transfer Characteristics," and European Pat. Pub. No. 377695 published as International Pat. Pub. No. WO1989011701 published Nov. 30, 2004 and entitled "Interrogation And Remote Control Device."

In use, at least one electrode of an implantable electrical stimulation device can be placed in the area of a BAT depot and be coupled to a signal generator. As will be appreciated by a person skilled in the art, the signal generator can have a variety of sizes, shapes, and configurations, and can be external to the patient or implanted therein similar to a cardiac pacemaker. The signal generator can create the electrical signal to be delivered to the BAT and can be on continuously once activated, e.g., manually, automatically, etc. The signal generator can be in electronic communication with a device external to the patient's skin to turn it on and off, adjust signal characteristics, etc. The external device can be positioned near the patient's skin, e.g., using a belt, a necklace, a shirt or other clothing item, furniture or furnishings such as a chair or a pillow, or can be a distance away from the patient's skin, such as a source located elsewhere in the same room or the same building as the patient. The electrical stimulation device can include circuitry configured to control an activation distance, e.g., how close to a power source the electrical stimulation device must be to be powered on and/or begin delivering electrical signals. Correspondingly, the external device can include a transmitter configured to transmit a signal to the electrical stimulation device's circuitry. If implanted, the signal generator can include an internal power source, e.g., a battery, a capacitor, stimulating electrodes, a kinetic energy source such as magnets positioned within wired coils configured to generate an electrical signal within the coils when shaken or otherwise moved, etc. In one embodiment, a battery can include a flexible battery, such as a Flexion battery available from Solicore, Inc. of Lakeland, Fla. In another embodiment, a battery can include an injectable nanomaterial battery. The power source can be configured to be recharged by transcutaneous means, e.g., through transcutaneous energy transfer (TET) or inductive coupling coil, and/or can be configured to provide power for an extended period of time, e.g., months or years, regardless of how long the power source is intended to provide power to the device. In some embodiments, a power source can be configured to provide power for less than an extended period of time, e.g., about 7 days, such as if a battery is replaceable or rechargeable and/or if device real estate can be conserved using a smaller, lower power battery. In some embodiments, the signal generator can include an electrode patch onboard configured to generate a pulse, thereby eliminating a need for a battery.

The signal generator, and/or any other portion of the device or external device, as will be appreciated by a person skilled in the art, can be configured to measure and record one or more physical signals relating to the activation of BAT. For non-limiting example, the physical signals can include voltage, current, impedance, temperature, time, moisture, salinity, pH, concentration of hormones or other chemicals, etc. The recorded physical signals can be presented to the patient's physician for evaluation of system performance and efficacy of brown adipose activation. Also, the recorded physical signals can be used in a closed-loop feedback configuration to allow the device, e.g., the controller, to dynamically adjust the electrical signal settings used for treatment.

In some embodiments, the BAT can be stimulated using a first electrical signal and a second electrical signal. The first electrical signal can be configured to stimulate the sympathetic nerves, and the second electrical signal can be configured to inhibit the other nerve type, e.g., to inhibit parasympathetic nerves and/or sensory nerves. Both of the first and second electrical signals can be delivered transcutaneously, which can facilitate application of the first and second electrical signals by allowing the first and second electrical signals to be delivered using the same device applied transcutaneously to a patient. In another embodiment, both of the first and second electrical signals can be directly delivered, which can allow for unobtrusive BAT stimulation. Embodiments of applying a first electrical signal to stimulate sympathetic nerves and applying a second electrical signal to inhibit another nerve type are further described in U.S. application Ser. No. 14/584,046 filed on Dec. 29, 2014 entitled "Methods And Devices For Inhibiting Nerves When Activating Brown Adipose Tissue," which is hereby incorporated by reference in its entirety.

BAT and the nerves innervating BAT can each be stimulated transcutaneously (e.g., from outside a patient's body) or directly (e.g., by direct contact therewith). For a subcutaneous example, a stimulator can be fully implanted within a patient to be in direct contact with a BAT depot to allow activation of the BAT depot. For another subcutaneous example, a stimulator can be fully implanted within a patient to be in direct contact with a nerve innervating a BAT depot to allow activation of the nerve. For a percutaneous example, a stimulator can be partially implanted within a patient to be in direct contact with a BAT depot to allow activation of the BAT depot, e.g., an external skin patch including at least one electrode positioned on a skin surface of a patient with at least one conductor extending from the at least one electrode and through the skin surface to the BAT depot, an external skin patch including at least one electrode positioned on a skin surface of a patient with at least one light-emitting fiber optic wire extending from the at least one electrode and through the skin surface to the BAT depot, etc. For another percutaneous example, a stimulator can be partially implanted within a patient to be in direct contact with a nerve innervating a BAT depot to allow activation of the nerve, e.g., an external skin patch including at least one electrode positioned on a skin surface of a patient with at least one conductive needle extending from the at least one electrode and through the skin surface to the nerve, an external skin patch including at least one electrode positioned on a skin surface of a patient with at least one light-emitting fiber optic wire extending from the at least one electrode and through the skin surface to the nerve, etc. For a transcutaneous example, a stimulator can be positioned external to a patient proximate a BAT depot to allow activation thereof, e.g., an external skin patch including at least one electrode positioned on a skin surface of a patient with a conductive gel coupled to the at least one electrode, etc.

The following examples provide methods and devices related to activating BAT using electrical energy. The invention is not necessarily limited by what is particularly shown and described in the following examples, except as indicated by the appended claims.

EXAMPLE 1

A study was performed using supraclavicular fat depots obtained from ten human cadaver subjects, six male and four female, with ages ranging from twenty-six to sixty-four (average age of 37.8 years), and with BMIs ranging from twenty to thirty-one (average BMI of 23).

Figure 12:
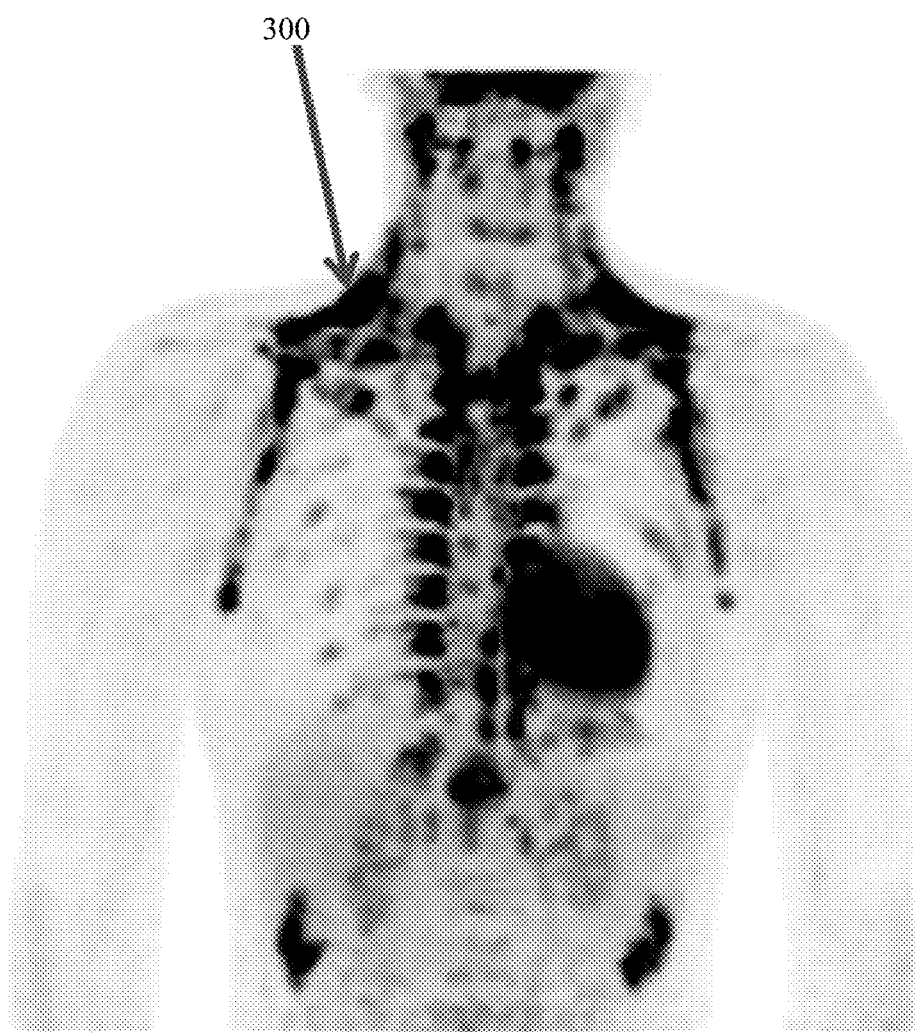
FIG. 12 is a schematic view of a PET-CT image showing the locations of BAT depots in a subject to a cold environment in an experiment.

FIG. 12 shows the site 300 of tissue sample collection from the subjects. FIG. 12 is a PET-CT scan of one of the subjects exposed to cold with black regions in the cold environment indicating BAT. BAT was found at this site 300 in seven of the ten cases. The three cases in which BAT was not found were in subjects over age sixty, thereby indicating a correlation of BAT presence in young people. As discussed further below, BAT was visually identified by confirming the presence of UCP1 indicative of BAT, and the presence of sympathetic nerve fibers was confirmed by evaluating tyrosine hydroxylase (TH) to determine the amount of noradrenergic nerves and visualize their distribution.

To collect the tissue samples from each of the subjects, the chest was opened and then the pericardial sac. Following the aorta pathway, the right brachiocephalic trunk was reached, and the supraclavicular fat depots were dissected out. The tissues were immediately immersed in paraformaldehyde (PFA) 4% and kept overnight at 4° C. The following day, the samples were analyzed at the gross anatomy level.

The average dimension of individual samples was about 3 cm. Each one of the samples was divided in 3-4 pieces of 1 $cm^3$ for the inclusion and the preparation of histological samples and consequent immune-histochemical analysis.

The following steps are dehydratation and paraffin embedding of the tissues for sectioning. Sections from three different levels (500 μm apart) were hematoxylin and eosin stained to assess morphology, immunohistochemistry, and morphometry. All of the observations were performed with a Nikon Eclipse 80i light microscope (Nikon, Japan).

For each section level, 3 μm-thick dewaxed sections were treated according to the avidin-biotin complex method (ABC) as follows: 1) endogenous peroxidase blocking with 3% hydrogen peroxide in methanol; 2) normal serum (1:75) for 20 min to reduce non-specific background; 3) incubation with primary antibodies (UCP1 and TH) overnight at 4° C.; 4) incubation with secondary IgG biotin-conjugated antibodies (1:200, Vector Labs, Burlingame, Calif.); 5) ABC kit (Vector Labs, Burlingame, Calif.); and 6) enzymatic reaction to reveal peroxidase with Sigma Fast 3,3'-diaminobenzidine as the substrate. Finally, sections were counterstained with hematoxylin and mounted in Eukitt (Fluka, Heidelberg, Germany).

Visible nerve bundles were observed to enter the fat pad. There were dissectible nerve bundles in close relationship with the fat collected in the supraclavicular area (close to the large blood vessels found in the lower neck). In the majority of the cases it was possible to isolate visible bundles in the big pieces of tissues. The presence of BAT was evaluated first by histology (H&E) searching for multilocular cells and then confirmed by immune-staining toward UCP1. Different degree of immune-reactivity were found in different subjects, ranging from small foci slightly positive for UCP1 to larger amount strongly positive for UCP1. This variability could be related to individual differences but it could be also in relation to different parameters (such as environmental conditions as well as technical issues in relation to the timing of the autoptic examination). However, the macroscopic appearance of the adipose tissue without BAT presence, displayed some common features with those in which BAT was actually found by histological examination. These tissues were built up by small lobuli and in particular the histology allow to visualize the smaller size of adipocytes in the core of the tissue. This is a possible intermediate step in the process of transformation of this tissue from a brown-like (found in younger people) to more white-like morphology (found in older people) and this is in agreement with recent data that describe a progressive loss of BAT in specific locations. This transformation is likely mainly due to a phenotypic switch from BAT toward WAT (transdifferentiation).

Similar to animal models (e.g., interscapular BAT of rats), nerves with different size in the human subjects were observed to enter the fat pad at supraclavicular location. The nerves were visualized in close proximity to the parenchyma and most likely have functional interaction with the adipose tissue itself. The nerves below 100 µm in diameter are strongly positive for TH (sympathetic fibers), and they are usually found around the big blood vessels of the tissue in interlobular position. Nerves above 100 µm (e.g., above 500 µm, in a range of 800-1000 µm, etc.) were observed to usually be negative for TH. Some of these nerves were observed to be partially positive for TH, likely because in bigger nerves, different nerve fiber types are present in different proportion, bearing sympathetic and sensory fibers. Visual estimates were that 80-90% of the fibers with a maximum dimension of 100 µm were positive for TH.

The observed sympathetic nerves were located in the BAT tissue. The diameters of the nerve fibers directly innervating BAT were identified as 0.14 µm+/−0.05 µm (n=87) for the axon diameters and as 0.60 µm+/−0.05 µm (n=238) for the varicosity diameters. The mean for all of the fibers was identified as 0.47 µm+/−0.33 µm. Based on the structure of the sympathetic nervous system, the fibers that were measured are postganglionic, small diameter, unmyelinated fibers.

EXAMPLE 2

Figure 13:
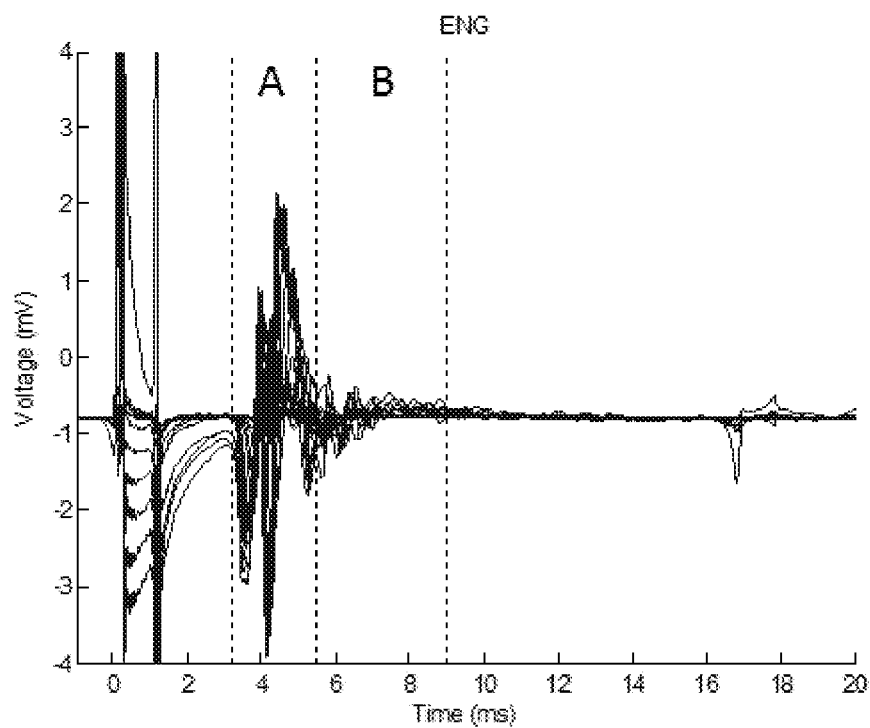
FIG. 13 is a graph showing an electroneurography graph of voltage versus time for a square wave in a transcutaneous stimulation of a tibial nerve in an animal model.
Figure 14:
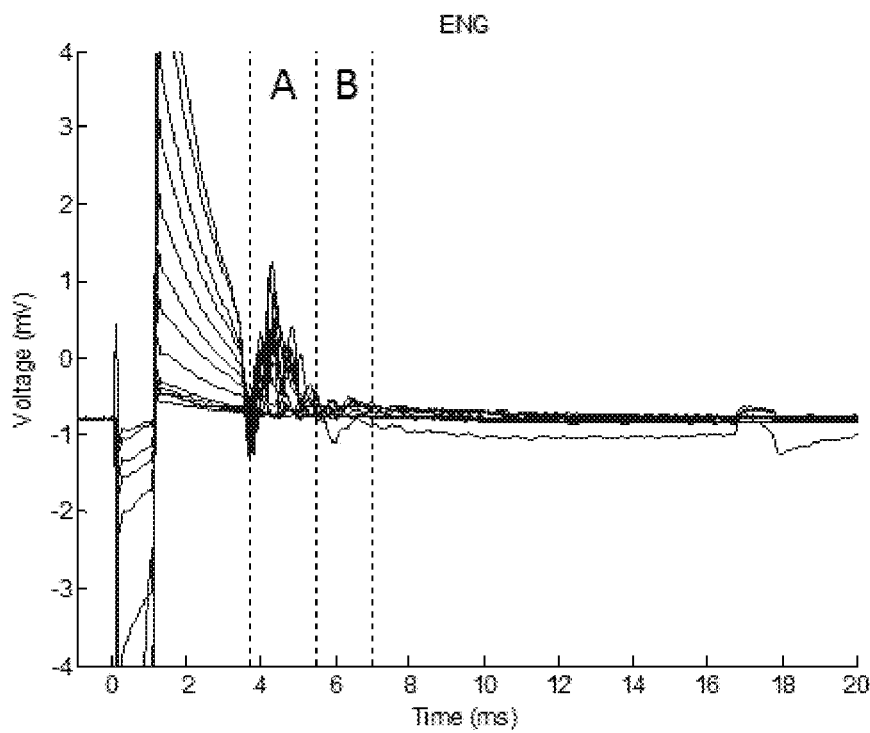
FIG. 14 is a graph showing an electroneurography graph of voltage versus time for SNS in a transcutaneous stimulation of a tibal nerve in an animal model.

A study was performed examining transcutaneous stimulation of the tibial nerve of dogs. The latency of the electroneurogram (ENG) response was used to calculate conduction velocity. The electrodes used were 1.25 in. diameter, round transcutaneous electrical nerve stimulation (TENS) electrodes covering a surface area was 7.92 cm$^2$. The fibers stimulated had diameters between 2 µm and 6 µm, e.g., myelinated fibers. The electrical signal applied had peak currents in a range of 50 mA to 300 mA. A maximum peak current of 300 mA was applied safely in this study because the dogs were anesthetized. A maximum peak current of 300 mA would ordinarily not be applied to a conscious subject, as it could cause discomfort. A maximum peak current to conscious subjects can be about 100 mA. Referring again to the study, the current density was in a range of 6.31 mA/cm$^2$ to 37.9 mA/cm$^2$. FIG. 13 shows electroneurography (ENG) of the square pulse applied. FIG. 14 shows the ENG of the sympathetic nervous system (SNS).

Table 1 below shows AB fiber thresholds for the tibial nerve transcutaneous stimulation.

TABLE 1

| | Peak Current Threshold (mA) | | | |
|---|---|---|---|---|
| | A-fibers | B-fibers | Avg + SD A | Avg + SD B |
| Square | 40 | 128 | 43 ± 31 | 85 ± 55 |
| | 13 | 23 | | |
| | 75 | 105 | | |
| SNS | 90 | 224 | 70 ± 47 | 134 ± 98 |
| | 16 | 30 | | |
| | 103 | 147 | | |

Table 2 below shows that the transcutaneous stimulation was able to stimulate nerve fibers having diameters of less than 2 µm. In Table 2, 20 m/s was the cutoff between A and B fibers, and the conversion factor used for the diameter was 5 m/s conduction velocity=1 µm diameter. Fibers of smaller diameter than those shown in Table 2 could be stimulated if electrode configuration is optimized.

TABLE 2

| Day | Wave | Electrode distance (cm) | A/B Fiber Cutoff (ms) | Activity latency (ms) | | Conduction velocity (m/s) | | Diameter (µm) | |
|---|---|---|---|---|---|---|---|---|---|
| | | | | min | max | min | max | min | max |
| Day 1 | Square | 12.5 | 6.25 | 4 | 13 | 9.6 | 31.3 | 1.9 | 6.3 |
| | SNS | | | 4 | 13 | 9.6 | 31.3 | 1.9 | 6.3 |
| Day 8 | Square | 11 | 5.5 | 3.2 | 9 | 12.2 | 34.4 | 2.4 | 6.9 |
| | SNS | | | 3.7 | 7 | 15.7 | 29.7 | 3.1 | 5.9 |
| Day 15 | Square | 12 | 6 | 3.5 | 9 | 13.3 | 34.3 | 2.7 | 6.9 |
| | SNS | | | 3.7 | 8 | 15.0 | 32.4 | 3.0 | 6.5 |
| | | | | | | | Average Square | 2.3 | 6.7 |
| | | | | | | | Average SNS | 2.7 | 6.2 |

CONCLUSION

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical method, comprising:
    generating an electrical signal that targets nerve fibers using fiber diameter selectivity; and
    delivering the electrical signal to brown adipose tissue (BAT), thereby activating nerve fibers having a first diameter.

2. The method of claim 1, wherein the delivered electrical signal does not activate nerve fibers having diameters that are different than the first diameter.

3. The method of claim 2, wherein the first diameter is less than about 2 μm; and
    the diameters that are different than the first diameter are greater than the first diameter and are less than about 6 μm.

4. The method of claim 2, wherein the nerve fibers having the first diameter are unmyelinated nerve fibers, and the nerve fibers having diameters that are different than the first diameter are myelinated nerve fibers.

5. The method of claim 1, wherein the first diameter is less than about 2 μm.

6. The method of claim 5, wherein the nerve fibers having the first diameter are sympathetic nerve fibers.

7. The method of claim 6, wherein the delivered electrical signal does not activate nerve fibers having diameters that are different than the first diameter; and
    the diameters that are different than the first diameter are greater than the first diameter and are less than about 6 μm.

8. The method of claim 7, wherein the nerve fibers having diameters that are different than the first diameter are parasympathetic nerve fibers.

9. The method of claim 1, wherein the electrical signal has a peak current that is in a range of about 50 mA to about 100 mA; and
    the electrical signal has a pulse width less than about 400 μs.

10. The method of claim 1, wherein the electrical signal has a current of about 10 mA.

11. The method of claim 1, wherein the generating includes continuously generating the electrical signal for at least one day such that the electrical signal is continuously delivered to the BAT for at least one day.

12. The method of claim 11, wherein the generating includes continuously generating the electrical signal for less than four weeks and such that the electrical signal is continuously delivered to the BAT for less than four weeks.

13. The method of claim 1, wherein the generating includes intermittently generating the electrical signal such that the electrical signal is intermittently delivered to the BAT.

14. A medical apparatus, comprising:
    a signal generator that generates the electrical signal of claim 1 using fiber diameter selectivity; and
    an electrode that delivers the electrical signal to the BAT.

15. A medical method, comprising:
    applying an electrical signal to brown adipose tissue (BAT) that targets nerves innervating the BAT using fiber diameter selectivity.

16. The method of claim 15, wherein the electrical signal activates first nerves innervating the BAT and having a first diameter without activating nerves innervating the BAT that have diameters different than the first diameter.

17. The method of claim 16, wherein the first diameter is less than about 2 μm; and
    the diameters different than the first diameter are greater than the first diameter and are less than about 6 μm.

18. The method of claim 16, wherein the first nerves are sympathetic nerves; and
    the nerves having diameters different than the first diameter are parasympathetic nerves.

19. A medical apparatus, comprising:
    a signal generator that generates the electrical signal of claim 15 using fiber diameter selectivity;
    wherein the electrical signal is applied to the BAT using an electrode.

20. The method of claim 19, wherein the first diameter is less than about 2 μm; and
    the diameters different than the first diameter are greater than the first diameter and are less than about 6 μm.

* * * * *